US010288563B1

(12) United States Patent
Ahmadivand et al.

(10) Patent No.: US 10,288,563 B1
(45) Date of Patent: May 14, 2019

(54) SENSOR PLATFORM BASED ON TOROIDAL RESONANCES FOR RAPID DETECTION OF BIOMOLECULES

(71) Applicants: Arash Ahmadivand, Miami, FL (US); Raju Sinha, Miami, FL (US); Burak Gerislioglu, Miami, FL (US); Nezih Pala, Fort Lauderdale, FL (US)

(72) Inventors: Arash Ahmadivand, Miami, FL (US); Raju Sinha, Miami, FL (US); Burak Gerislioglu, Miami, FL (US); Nezih Pala, Fort Lauderdale, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/876,481

(22) Filed: Jan. 22, 2018

(51) Int. Cl.
*G01N 21/552* (2014.01)
*G01N 33/569* (2006.01)
*G01N 21/3581* (2014.01)

(52) U.S. Cl.
CPC ....... *G01N 21/554* (2013.01); *G01N 21/3581* (2013.01); *G01N 33/56983* (2013.01); *G01N 2333/185* (2013.01)

(58) Field of Classification Search
CPC ............. G01N 21/554; G01N 21/3581; G01N 33/56983; G01N 2333/185
See application file for complete search history.

(56) References Cited

U.S. PATENT DOCUMENTS 9,739,710 B2 * 8/2017 Schubert ................ G01N 21/47
2016/0084702 A1 * 3/2016 Tomioka ............ G01N 21/3581
250/338.3
2016/0131585 A1 * 5/2016 Xiong .................... B82Y 15/00
436/74

OTHER PUBLICATIONS

Lin et al. Langmuir 2002, 18, 788-796 (Year: 2002).*
Wei et al. (IEEE Microwave and wireless components letters, vol. 26, No. 2, Feb. 2016) (Year: 2016).*
Koray Aydin et al. (2005 New J Phys. 7 168) (Year: 2005).*
Ouedraogo et al. (IEEE Antennas and Wireless Propagation Letters, vol. 9, pp. 75-78, 2010) (Year: 2010).*
Mohammady et al. (Journal of Microwaves, Optoelectronics, and Electromagnetic Applications vol. 16, No. 2 Sao Caetano do Sul Apr./Jun. 2017) (Year: 2017).*
Lee et al. 2015 J Opt. 17 025103. (Year: 2015).*
Zijlstra et al., "Optical detection of single non-absorbing molecules using the surface plasmon resonance of a gold nanorod," Nature Nanotechnology, Apr. 2012, pp. 379-382, vol. 7.
Ashkin et al., "Optical trapping and manipulation of viruses and bacteria," Science, Mar. 1987, pp. 1517-1520, vol. 235.
(Continued)

*Primary Examiner* — Sally A Merkling
(74) *Attorney, Agent, or Firm* — Saliwanchik, Lloyd & Eisenschenk

(57) ABSTRACT

A plasmonic resonator can include: a substrate; a central resonator on the substrate; a first curved resonator disposed on the substrate and disposed at a first side of the central resonator; and a second curved resonator disposed on the substrate and disposed at a second side of the central resonator, the first curved resonator and the second curved resonator being asymmetric to each other with respect to the central resonator, and the central resonator and at least one of the first and second curved resonators being made of different materials.

18 Claims, 13 Drawing Sheets

(56) References Cited

OTHER PUBLICATIONS

Kuznetsov et al., "Laser fabrication of large-scale nanoparticle arrays for sensing applications," ACS Nano, May 2011, pp. 4843-4849, vol. 5, No. 6.
Chang et al., "A plasmonic fano switch," Nano Letters, Aug. 2012, pp. 4977-4982, vol. 12.
Ott et al., "Lorentz meets fano in spectral line shapes: a universal phase and its laser control," Science, May 2013, pp. 716-720, vol. 340.
Gupta et al., "Toroidal versus fano resonances in high Q planar THz metamaterials," Advanced Optical Materials, Sep. 2016, pp. 2119-2125, vol. 4.
Jackson, "Multipole fields," Classical Electrodynamics, Aug. 1998, pp. 739-779, Wiley.
Afanasiev et al., "Electromagnetic properties of a toroidal solenoid," Journal of Physics A: Mathematical and General, Apr. 1992, pp. 4869-4886, vol. 25.
Ye et al., "The magnetic toroidal dipole in steric metamaterial for permittivity sensor application," Physica Scripta, Oct. 2013, pp. 1-5, vol. 88, No. 055002.
Ordal et al., "Optical properties of Al, Fe, Ti, Ta, W, and Mo at submillimeter wavelengths," Applied Optics, Mar. 1988, pp. 1203-1209, vol. 27, No. 6.
Lynch et al., "Introduction to the data for several metals," Handbook of Optical Constants of Solids, Nov. 1997, pp. 240-249, Academic Press.
Newton, Scattering Theory of Waves and Particles—Second Edition, Jun. 2013, pp. 48-78, Springer-Verlag.
Zhang et al., "Liquid-crystal-filled photonic crystal for terahertz switch and filter," Journal of the Optical Society of America B, Dec. 2008, pp. 101-106, vol. 26, No. 1.
Zhang et al., "Terahertz filters based on frequency selective surfaces for high-speed terahertz switch," Journal of Applied Physics, Jan. 2013, pp. 1-4, vol. 113, No. 014504.
Maier et al., "Plasmonics—a route to nanoscale optical devices," Advanced Materials, Oct. 2001, pp. 1501-1505, vol. 13, No. 19.
Lindquist et al., "Engineering metallic nanostructures for plasmonics and nanophotonics," Reports on Progress in Physics, Mar. 2012, pp. 1-119, Author Manuscript.
Anker et al., "Biosensing with plasmonic nanosensors," Nature Materials, Jun. 2008, pp. 442-453, vol. 7.
Dondapati et al., "Label-free biosensing based on single gold nanostars as plasmonic transducers," ACS Nano, Oct. 2010, pp. 6318-6322, vol. 4, No. 11.
Kravets et al., "Singular phase nano-optics in plasmonic metamaterials for label-free single-molecule detection," Nature Materials, Jan. 2013, pp. 304-309, vol. 12.
Fischer et al., "Far-infrared vibrational modes of DNA components studied by terahertz time-domain spectroscopy," Physics in Medicine and Biology, Oct. 2002, pp. 3807-3814, vol. 47.
Berrier et al., "Selective detection of bacterial layers with terahertz plasmonic antennas," Biomedical Optics Express, Oct. 2012, pp. 2937-2949, vol. 3, No. 11.
Menikh et al., "Terahertz biosensing technology: frontiers and progress," Chemphyschem, Aug. 2002, pp. 655-658, vol. 3.
Park et al., "Detection of microorganisms using terahertz metamaterials," Scientific Reports, May 2014, pp. 1-7, vol. 4, No. 4988.
Ferguson et al., "Materials for terahertz science and technology," Nature Materials, Sep. 2002, pp. 26-33, vol. 1.
Mickan et al., "Label-free bioaffinity detection using terahertz technology," Physics in Medicine and Biology, Oct. 2002, pp. 3789-3795, vol. 47.
Nagel et al., "THz biosensing devices: fundamentals and technology," Journal of Physics: Condensed Matter, Apr. 2006, pp. S601-S618, vol. 18.
Tao et al., "Performance enhancement of terahertz metamaterials on ultrathin substrates for sensing applications," Applied Physics Letters, Dec. 2010, pp. 1-3, vol. 97, No. 261909.
Wu et al., "Fano-resonant asymmetric metamaterials for ultrasensitive spectroscopy and identification of molecular monolayers," Nature Materials, Nov. 2011, pp. 69-75, vol. 11.
Musso et al., "Detection of zika virus in saliva," Journal of Clinical Virology, Jul. 2015, pp. 53-55, vol. 68.
Saxena et al., "Zika virus outbreak: an overview of the experimental therapeutics and treatment," VirusDis, Feb. 2016, pp. 111-115, vol. 27, No. 2.
Vorou, "Letter to the editor: diagnostic challenges to be considered regarding zika virus in the context of the presence of the vector Aedes albopictus in europe," Euro Surveillance, Mar. 2016, pp. 1-2.
Song et al., "Instrument-free point-of-care molecular detection of zika virus," Analytical Chemistry, Jun. 2016, pp. 7289-7294, vol. 88.
Kaushik et al., "Electrochemical biosensors for early stage zika diagnostics," Trends in Biotechnology, Apr. 2017, pp. 1-10.
Gallinet et al., "Influence of electromagnetic interactions on the line shape of plasmonic fano resonances," ACS Nano, Oct. 2011, pp. 8999-9008, vol. 5, No. 11.
Singh et al., "The fano resonance in symmetry broken terahertz metamaterials," IEEE Transactions on Terahertz science and technology, Nov. 2013, pp. 1-7, vol. 3, No. 6.
Yanik et al., "Seeing protein monolayers with naked eye through plasmonic fano resonances," PNAS, Jul. 2011, pp. 11784-11789, vol. 108, No. 29.
Wang et al., "Double fano resonances due to interplay of electric and magnetic plasmon modes in planar plasmonic structure with high sensing sensitivity," Optics Express, Jan. 2013, pp. 2236-2244, vol. 21, No. 2.
Gu et al., "Active control of electromagnetically induced transparency analogue in terahertz metamaterials," Nature Communications, Oct. 2012, pp. 1-6, vol. 3, No. 1151.
Mario et al., "Asymmetric fano resonance and bistability for high extinction ratio, large modulation depth, and low power switching," Optics Express, Dec. 2006, pp. 12770-12781, vol. 14, No. 26.
Yu et al., "High quality factor metallodielectric hybrid plasmonic-photonic crystals," Advanced Functional Materials, May 2010, pp. 1910-1916, vol. 20.
Cao et al., "Low-loss ultra-high-Q dark mode plasmonic fano metamaterials," Optics Letters, Aug. 2012, pp. 3366-3368, vol. 37, No. 16.
Singh et al., "Ultrasensitive terahertz sensing with high-Q fano resonances in metasurfaces," Applied Physics Letters, Oct. 2014, pp. 1-5, vol. 105, No. 171101.
Fedotov et al., "Resonant transparency and non-trivial non-radiating excitations in toroidal metamaterials," Scientific Reports, Oct. 2013, pp. 1-5, vol. 3, No. 2967.
Liu et al., "Efficient excitation and tuning of toroidal dipoles within individual homogenous nanoparticles," Optics Express, Sep. 2015, pp. 24738-24747, vol. 23, No. 19.
Kaelberer et al., "Toroidal dipolar response in a metamaterial," Science, Dec. 2010, pp. 1510-1512, vol. 330.
Gupta et al., "Sharp toroidal resonances in planar terahertz metasurfaces," Advanced Materials, Jul. 2016, pp. 1-6.
Papasimakis et al., "Electromagnetic toroidal excitations in matter and free space," Nature Materials, Feb. 2016, pp. 263-271, vol. 15.
Dubovik et al., "Toroid moments in electrodynamics and solid-state physics," Physics Reports, Mar. 1990, pp. 145-202, vol. 187, No. 4.
Fan et al., "Low-loss and high-Q planar metamaterial with toroidal moment," Physical Review B, Mar. 2013, pp. 1-5, vol. 87, No. 115417.
Savinov et al., "Toroidal dipolar excitation and macroscopic electromagnetic properties of metamaterials," Physical Review B, May 2014, pp. 1-12, vol. 89, No. 205112.
Wu et al., "Magnetic iron oxide nanoparticles: synthesis and surface functionalization strategies," Nanoscale Research Letters, Oct. 2008, pp. 397-415, vol. 3.
Zhu et al., "Switchable magnetic metamaterials using micromachining processes," Advanced Materials, Feb. 2011, pp. 1-5.
Meng et al., "Polarization-independent metamaterial analog of electromagnetically induced transparency for a refractive-index-based sensor," IEEE Transactions on Microwave Theory and Techniques, Oct. 2012, pp. 3013-3022, vol. 60, No. 10.

(56) References Cited

OTHER PUBLICATIONS

Dong et al., "Enhanced sensing performance by the plasmonic analog of electromagnetically induced transparency in active metamaterials," Applied Physics Letters, Sep. 2010, pp. 1-3, vol. 97, No. 114101.

Ahmadivand et al., "Tailoring the negative-refractive-index metamaterials composed of semiconductor-metal-semiconductor gold ring/disk cavity heptamers to support strong fano resonances in the visible spectrum," Journal of the Optical Society of America A, Feb. 2015, pp. 204-212, vol. 32, No. 2.

Currie, "Detection and quantification limits: origins and historical overview," Analytica Chimica Acta, May 1999, pp. 127-134, vol. 391.

Sinha et al., "Tunable room temperature THz sources based on nonlinear mixing in a hybrid optical and THz micro-ring resonator," Scientific Reports, Mar. 2015, pp. 1-8, vol. 5, No. 9422.

Sinha et al., "Tunable, room temperature CMOS-compatible THz emitters based on nonlinear mixing in microdisk resonators," Journal of Infrared, Millimeter, and Terahertz Waves, Nov. 2015, pp. 1-13.

\* cited by examiner

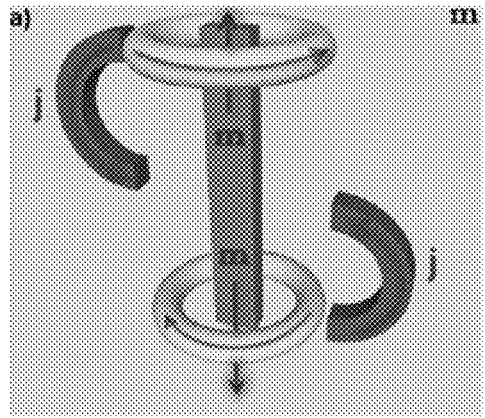
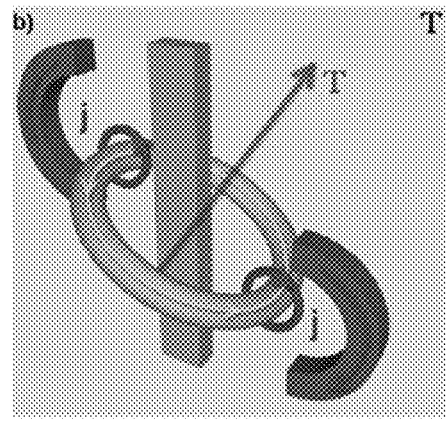
Figure 3(a)  Figure 3(b)
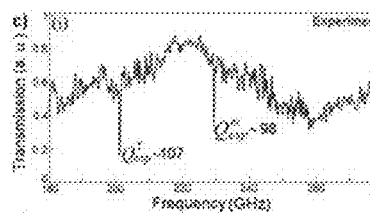 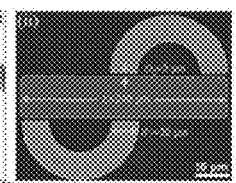 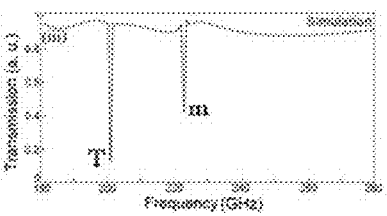
Figure 3(c)
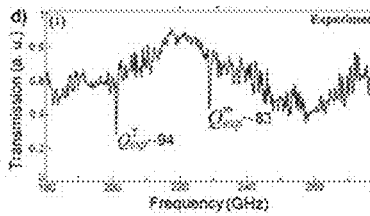 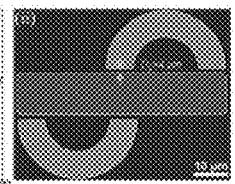 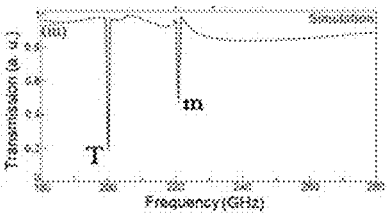
Figure 3(d)
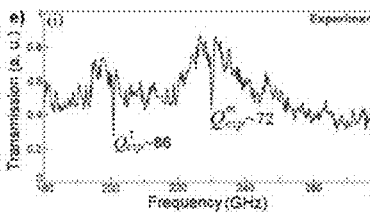 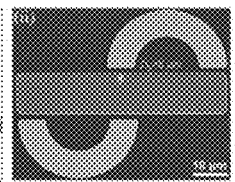 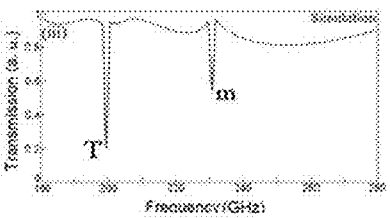
Figure 3(e)

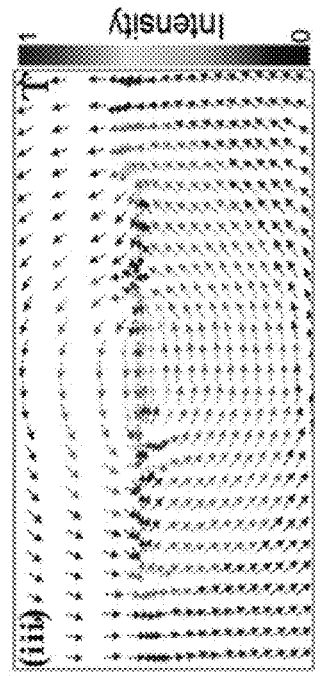
Figure 4(a)(i)   Figure 4(a)(ii)   Figure 4(a)(iii)
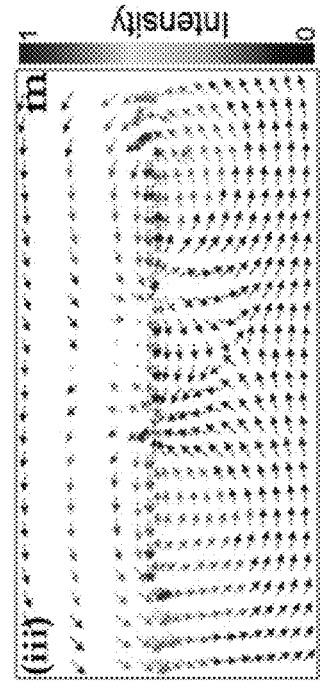
Figure 4(b)(i)   Figure 4(b)(ii)   Figure 4(b)(iii)

SENSOR PLATFORM BASED ON TOROIDAL RESONANCES FOR RAPID DETECTION OF BIOMOLECULES

STATEMENT OF GOVERNMENT SUPPORT

This invention was made with government support under Grant No. W911NF-12-2-0023 awarded by Army Research Laboratory (ARL) Multiscale Multidisciplinary Modeling of Electronic Materials (MSME) Collaborative Research Alliance (CRA) and Award No. 1160483 awarded by National Science Foundation Nanosystems Engineering Research Center for Advanced Self-Powered Systems of Integrated Sensors and Technologies (ASSIST). The government has certain rights in the invention.

BACKGROUND

Manipulation and active control of an incident intense radiation by metallic objects have been demonstrated using localization of plasmons in subwavelength dimensions ([1], [2]). Providing real-time spectral response control plasmonics has emerged as a promising technology for tailoring fast, efficient, and tightly integrated nanodevices for photonic applications ([1], [2], [3]). Rising demands for miniaturized and multifunctional all-optical devices requires advances in integration of the next generation of photonic circuits. Among several potential applications of plasmonics technology, the biomedical applications still need to be improved for quick infection diagnosis and real-time pharmacology purposes ([4], [5], [6]). Plasmonic metasurfaces with exotic electromagnetic response have been relatively better developed for advanced label-free detection in biosensing applications in the spectral ranges from near-infrared wavelengths ([7]) to the terahertz (THz) ([8], [9]) and microwave ([10], [11]) frequencies. It is well-accepted that THz frequencies are highly compatible with human tissues due to absence of ionization hazard because of their low energy of the incident radiation (in the range of a few meV) ([8], [9], [12], [13]). This spectacular advantage of THz plasmonic structures accompanied with cost-effective and easy microfabrication techniques (photolithography) have stimulated researchers to exploit THz plasmonics for immunosensing applications ([14], [15]).

As a promising technique, THz spectroscopy allows for non-invasive, non-contact, non-destructive, and label-free biomarker detection and therefore attracts growing interest for biomedical and clinical applications ([15], [16], [17], [18], [19]). It is shown that electromagnetic field enhancement and confinement by metallic THz components facilitate detection of targeted bio-agents such as specific proteins, antibodies, and etc., ([9], [16], [17], [19], [20], [21]). Despite of such a unique potential, the selectivity and sensitivity of THz metasurfaces for immunosensing sensing applications have not been analyzed comprehensively due to mismatch between resonance frequency of nanoscale biotargets and metasurfaces. This is because of non-responsivity of micro- and nano-organisms with the size of approximately ~λ/100, causing to be almost transparent to the incident radiation, therefore, reflect poor scattering cross-section ([22]). This challenge in THz metamaterials can be circumvented using two approaches: 1) introducing nano-size particles (e.g. nanospheres) ([9], [23]) on the microscale plasmonic chips to trap and bind biological objects and monitor their effect on the spectral response, and 2) excitation of ultrasharp antisymmetric resonances (with high-Q-factors) to show super-sensitivity to the small environmental variations. Here, by using the high-Q advantage of magnetic dipolar toroidal moment, the behavior of this mode is analyzed for the presence of Zika-virus (ZIKV) envelope protein and its specific antibody. Zika is a new medical threat across the world as an infectious disease which causes serious health disorders, possibly leading to death ([24], [25]). Various methods have been introduced and conducted for practical detection of this type of infection such as reverse transcriptase-PCR ([26]), antibody-based methods (e.g. ELISA) ([26]), point-of-care (POC) molecular detection ([27]), and electrochemical biosensing ([28]). Despite of the growing research, most of these applications suffer from high-costs, lack of sensitivity and repeatability, and complex processing. Therefore, providing an all-optical microscale metasurface with an ability to detect picomolar concentrations of ZIKV envelope protein would help us to tailor practical, easy to fabricate, and accurate detection mechanism with high reliability.

The exquisite properties of plasmonic structures with symmetric and antisymmetric geometries allow for achieving spectral line shapes as pronounced resonant modes in the optical band reaching to the far-infrared region (FIR) ([29], [30]). The response of these resonant modes to the polarization variations of incident radiation and physical changes in their surrounding medium have triggered development of fast switches and high-precision sensors ([31], [32], [33]). Recently, successful examples of plasmonic line shapes have been introduced for practical photoswitching applications based on Fano-resonant metallic assemblies ([34]), asymmetric line shapes in Mach-Zehnder interferometers ([35]), electromagnetically induced transparency (EIT) ([33]), and Lorentzian spectral line shapes ([36]). The corresponding linewidth of these resonant modes is defined by full-width at half-maximum (FWHM), known as quality-factor (Q-factor) ([37]). The sharpness and depth of these resonance line shapes play crucial role for developing advanced high-Q integrated devices ([38], [39]). However, sustaining strong resonance coupling between optically excited modes in planar 2D structures is difficult and achieving ultrasharp and substantially high-Q factor line shapes is a serious challenge.

Recent analyses have shown that plasmonic metasurfaces composed of 3D ([40], [41], [42]), and 2D ([43], [44]) unit cells can be tailored to support distinct toroidal multipolar modes which are categorized in different resonant modes family far from the classical electromagnetic modes ([45]). These hardly distinguishable modes can be identified as the magnetic multipoles that are condensed into a single spot corresponding to a unique current density ([43], [44], [45], [46]). In the toroidal moment limit, oscillating radial components of the current density are included in the radiative fields, giving rise to the formation of a unique family of dynamic toroidal multipolar modes ([42], [47]). Toroidal dipolar resonant mode has been observed in 3D structures, however, challenging and complex fabrication processes limit their practical applications ([43], [48], [49], [50], [51]). Therefore, excitation of toroidal multipolar modes in planar 2D structures has received growing attention recently due to their easy fabrication and characterization ([43]-[51]). The primary problem with 2D structures is the inherently weak coupling of magnetic fields at the dielectric spacer of the resonators, which makes detecting the magnetic toroidal modes very difficult. Confinement of the incident magnetic field inside a unit cell into a rotating torus loop is another problem correlating with planar structures.

BRIEF SUMMARY

Embodiments of the subject invention provide novel and advantageous plasmonic resonators that comprise a titanium (Ti) rectangular central resonator and an iron (Fe) curved resonator, thereby providing high-Q factor and providing a platform for an immunosensor (e.g., for the Zika virus).

In an embodiment, a plasmonic resonator unit cell can comprise: a central resonator; a first curved resonator disposed at a first side of the central resonator; and a second curved resonator disposed at a second side of the central resonator, the first curved resonator and the second curved resonator being asymmetric to each other with respect to the central resonator.

In another embodiment, a plasmonic resonator can comprise: a substrate; a central resonator on the substrate; a first curved resonator disposed on the substrate and disposed at a first side of the central resonator; and a second curved resonator disposed on the substrate and disposed at a second side of the central resonator, the first curved resonator and the second curved resonator being asymmetric to each other with respect to the central resonator, and the central resonator and at least one of the first and second curved resonators being made of different materials.

In yet another embodiment, a plasmonic resonator system can comprise: a silicon substrate having a crystal orientation of <100>; and a plurality of plasmonic resonators on the silicon substrate, each of the plurality of plasmonic resonators comprising: a Ti rectangular central resonator on the silicon substrate; a first Fe curved resonator disposed on the silicon substrate and disposed at a first side of the Ti rectangular central resonator; and a second Fe curved resonator disposed on the silicon substrate and disposed at a second side of the Ti rectangular central resonator, a first end of the first Fe curved resonator corresponding to a first longitudinal end of the Ti rectangular central resonator, a second end of the first Fe curved resonator corresponding to a center of the Ti rectangular central resonator, a first end of the second Fe curved resonator corresponding to the center of the Ti rectangular central resonator, and a second end of the second Fe curved resonator corresponding to a second longitudinal end of the Ti rectangular central resonator, and each of the second end of the first Fe curved resonator and the first end of the second Fe curved resonator being spaced apart from the Ti rectangular central resonator by an offset gap.

BRIEF DESCRIPTION OF DRAWINGS

FIG. 3(a) shows a schematic of a magnetic resonance around a plasmonic resonator unit cell according to an embodiment of the subject invention.

FIG. 3(b) shows a schematic of a toroidal resonance around a plasmonic resonator unit cell according to an embodiment of the subject invention.

FIG. 3(c) shows an electromagnetic response of a plasmonic resonator unit cell having an offset gap of 3 µm.

FIG. 3(d) shows an electromagnetic response of a plasmonic resonator unit cell having an offset gap of 4 µm.

FIG. 3(e) shows an electromagnetic response of a plasmonic resonator unit cell having an offset gap of 5 µm.

FIG. 4(a)(i) shows a local H field snapshot for a toroidal resonance in linear scales in a plasmonic resonator unit cell according to an embodiment of the subject invention.

FIG. 4(a)(ii) shows a local H field snapshot for a toroidal resonance in logarithmic scales in a plasmonic resonator unit cell according to an embodiment of the subject invention.

FIG. 4(a)(iii) shows a vectorial map for the magnetic field lines of toroidal resonant mode in a plasmonic resonator unit cell according to an embodiment of the subject invention.

FIG. 4(b)(i) shows a local H field snapshot for a magnetic resonance in linear scales in a plasmonic resonator unit cell according to an embodiment of the subject invention.

FIG. 4(b)(ii) shows a local H field snapshot for a magnetic resonance in logarithmic scales in a plasmonic resonator unit cell according to an embodiment of the subject invention.

FIG. 4(b)(iii) shows a vectorial map for the magnetic field lines of magnetic resonant mode in a plasmonic resonator unit cell according to an embodiment of the subject invention.

FIG. 9(a) shows toroidal response frequency shifts due to conjugated ZIKV protein concentration and fitting line.

FIG. 9(b) shows transmission spectra for a plasmonic chip characterized for three days.

DETAILED DESCRIPTION

Figure 1A:
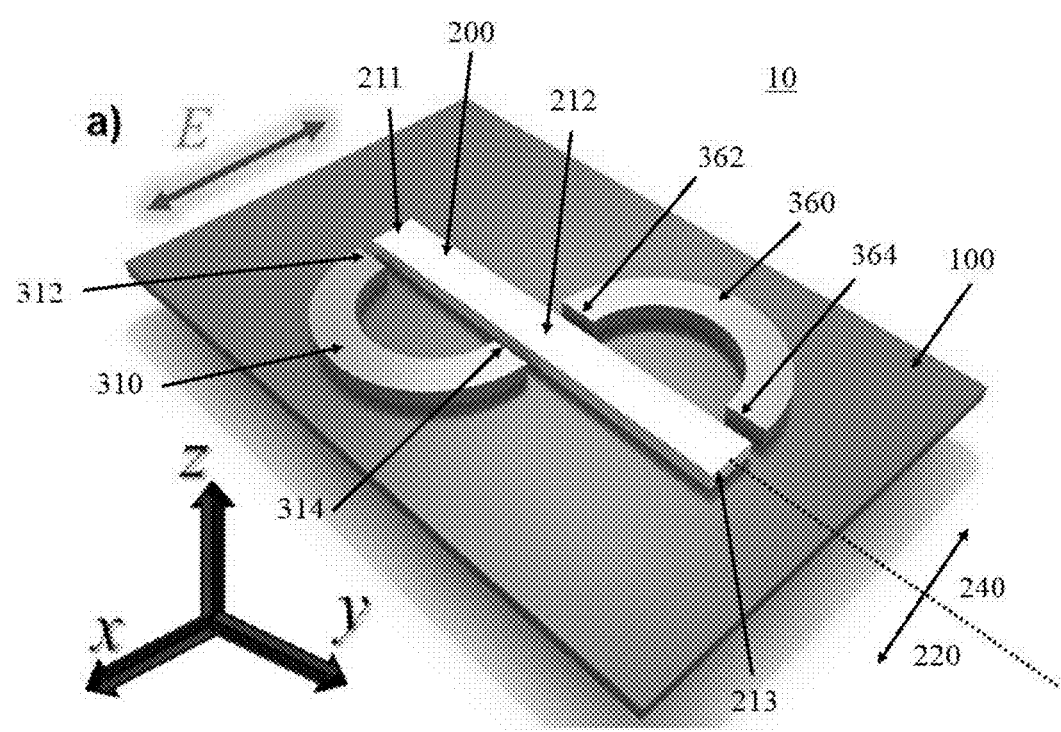
FIG. 1(a) shows a perspective view of a plasmonic resonator unit cell according to an embodiment of the subject invention.

Embodiments of the subject invention provide novel and advantageous plasmonic resonators that comprise a titanium (Ti) rectangular central resonator and an iron (Fe) curved resonator, thereby providing high-Q factor and providing a platform for an immunosensor (e.g., for the Zika virus (ZIKV)).

Rapid and accurate detection of biomolecules such as virus proteins is utterly important for early and accurate diagnosis of epidemic and contagious infections which can help effectively prevent indomitable distribution of diseases and secure the public health. For instance, as an international ongoing threat, Zika-virus has been announced as an epidemic and wide spreading infection, causing terrible microcephaly and neurological syndromes. Embodiments of the subject invention provide a platform for early stage diagnostics of ZIKV for very low concentrations of infection. The presented all-optical immunosensing system based on the embodiments of the subject invention is fast, precise, cost-effective, non-invasive, and easy to use. In an embodiment, a system can comprise a metallic structure that provides ultra-strong magnetic plasmonic resonances at the terahertz domain with ultrasensitivity to the presence of infection-related protein with its respective antibody. Moreover, the sensors of embodiments of the subject invention provide stability and repeatability features by keeping the accuracy acceptable at low concentrations in the range of a few concentrations on infection in the analyzed sample.

The sensing platform of embodiments of the subject invention can be effectively used for rapid detection of many biomolecules including ZIKV which would allow early detection of various infections with high accuracy, low-costs, and reliability for advanced clinical applications. The commercial applications include, but not limited to, biochemical sensing and detection for clinical and medical diagnosis, food and environmental safety, and drug discovery.

The micro-structures of embodiments of the subject invention comprise iron (Fe) and titanium (Ti) components acting as magnetic resonators and torus, respectively. The structures allow for excitation of toroidal dipoles in the terahertz (THz) domain with the experimental Q-factor of ~107. Taking the advantage of high-Q toroidal line shape and its dependence on the environmental perturbations, the embodiments show that room-temperature toroidal plasmonic metasurface is a reliable platform for immunosensing applications. The plasmonic metasurface of the subject invention is used to detect Zika-virus (ZIKV) envelope protein using a specific ZIKV antibody. The sharp toroidal resonant modes of the surface functionalized structures shift as a function of the ZIKV protein for very small concentrations (~picoMolar (pM)). The results of sensing experiments reveal rapid, accurate and quantitative detection of proteins with the limit of detection of ~24.2 picograms/milliliter (pg/mL) and sensitivity of 6.47 GHz/log(pg/mL).

In embodiments of the subject invention, by going beyond the conventional plasmonic platforms, 2D micro-structures comprising iron (Fe) and titanium (Ti) for the magnetic and electric resonators, respectively, can be used to design a set of asymmetric split resonators as meta-atoms to support ultrastrong and narrow magnetic toroidal moments in the THz spectrum. With coupled-resonator effect, the magnetic nature of Fe helps intensify resonating magnetic field at the central block of the plasmonic structure. Therefore, the middle Ti rectangle resonator acts as a meridian for oscillation of circular and close-loop head-to-tail array of magnetic dipoles. This effect makes the toroidal response line shape extremely sharp, narrow and deep. Taking the advantage of superb sharp toroidal moment, it is considered the sensitivity of this dip to the presence of a specific protein attached to the plasmonic system. The target protein can be selected as the Zika virus protein (ZIKV) which recently outspreaded causing epidemic disorders such as microcephaly and neurological effects. The embodiment provides an all-optical platform for direct detection of ZIKV envelope protein successfully by using a plasmonic THz metasurface via monitoring the behavior of the toroidal moment. In addition to accurate detection of ZIKV protein with the concentration of picomolar (pM) using its respective antibodies, the embodiments show the sensitivity, repeatability, reliability, and accuracy of the toroidal THz plasmonic sensor.

Figure 1B:
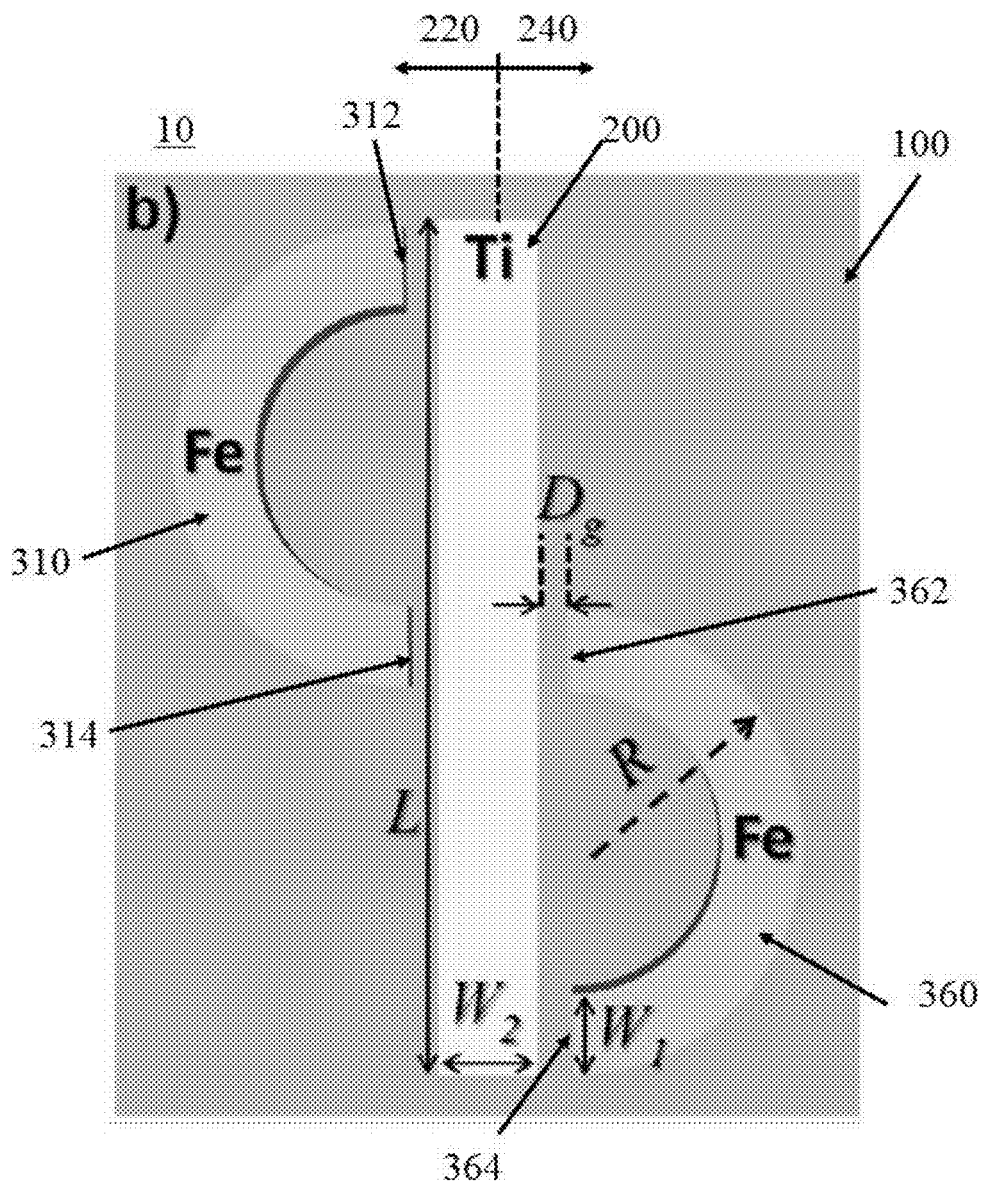
FIG. 1(b) shows a top view of a plasmonic resonator unit cell according to an embodiment of the subject invention.
Figures 1C, 1D:
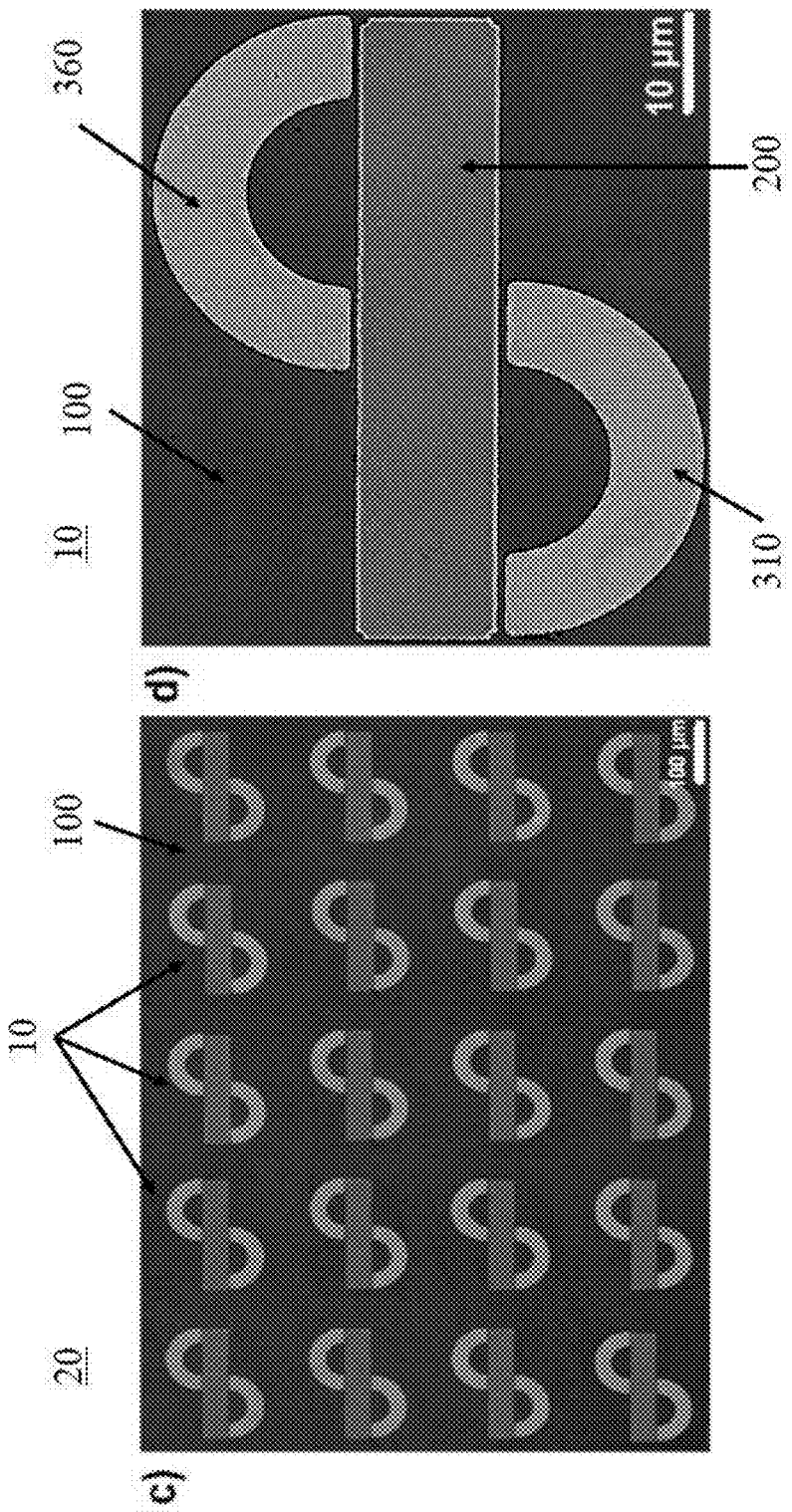
FIG. 1(c) shows a top view of a plasmonic resonator system according to an embodiment of the subject invention.
FIG. 1(d) shows a Scanning Electron Microscope (SEM) image of a plasmonic resonator unit cell according to an embodiment of the subject invention.

FIGS. 1(a) and 1(b) show a perspective view and a top view of a plasmonic resonator unit cell according to an embodiment of the subject invention, respectively. FIG. 1(c) shows a top view of a plasmonic resonator system including an array of the plasmonic resonator unit cells according to an embodiment of the subject invention, and FIG. 1(d) shows a Scanning Electron Microscope (SEM) image of a plasmonic resonator unit cell according to an embodiment of the subject invention. In particular, FIG. 1(a) shows the schematic view of the planar micro-assembly unit on a silicon host with the incident THz beam direction and electric field polarization. The geometrical and material descriptions of the resonators and components are demonstrated in a top-view profile in FIG. 1(b). FIG. 1(c) exhibits an SEM image of the fabricated compositional unit cell arrays on a high-resistivity silicon wafer with the gap distance of $D_g=3$ μm between peripheral and central resonators. The magnified SEM image of the planar plasmonic unit cell is presented in FIG. 1(d). The plasmonic resonator can comprise an oxide layer made of a few nanometers natural oxide ($Fe_2O_3$) on the Fe structures at room temperature. By launching a THz beam in −z direction in FIG. 1(a), the excited local modes lead to formation of circular magnetic fields in the central zone of the peripheral curved structures. This results in dramatic suppression in the electric dipole moment by the excited magnetic and toroidal resonances. The suppressed dipolar moment is associated with the strong electric resonant mode arising from the central resonator and the weak modes in the curved split resonators.

Referring to FIGS. 1(a)-1(d), a plasmonic resonator unit cell 10 comprises a substrate 100, a central resonator 200 disposed on the substrate 100, a first curved resonator 310 disposed on the substrate 100 and disposed at a first side 220 of the central resonator 200, and a second curved resonator 360 disposed on the substrate 100 and disposed at a second side 240 of the central resonator 200. The first curved resonator 310 is located to face an upper portion of the central resonator 200 and the second curved resonator 360 is located to face a lower portion of the central resonator 200. That is, the first curved resonator 310 and the second curved resonator 360 are arranged to be asymmetric to each other with respect to the central resonator 200.

The central resonator 200 has a rectangular shape including a first longitudinal end 211 and a second longitudinal end 213 at both ends in a longitudinal direction parallel to y direction. In addition, the central resonator 200 further comprises a center 212 between the first longitudinal end 211 and the second longitudinal end 213.

The first curved resonator 310 and the second curved resonator 360 are arranged at both sides 220 and 240 such that the first curved resonator 310 and the second curved resonator 360 are not arranged at one straight line in x direction perpendicular to the y direction. In particular, a first end 312 of the first curved resonator 310 corresponds to the first longitudinal end 211 of the central resonator 200, a second end 314 of the first curved resonator 310 corresponds to the center 212 of the central resonator 200, a first end 362 of the second curved resonator 360 corresponds to the center 212 of the central resonator 200, and a second end 364 of the second curved resonator 360 corresponds to the second longitudinal end 213 of the central resonator 200.

Each of the first curved resonator 310 and the second curved resonator 360 can be curved to have the same radius R. The second end 314 of the first curved resonator 310 and the first end 362 of the second curved resonator 360 are spaced apart from the central resonator 200 by an offset gap $D_g$. Each of the first curved resonator 310 and the second curved resonator 360 has a first width $W_1$, and the central resonator 200 has a second width $W_2$ and a length L. The embodiments of FIGS. 1(c) and 1(d) show a plasmonic resonator including the central resonator 200 having the length L of 240 μm and the second width $W_2$ of 40 μm, and the first 310 and second 360 curved resonators having the first width $W_1$ of 30 μm and the radius R of 50 μm, wherein the first 310 and second 360 curved resonators are spaced apart from the central resonator 200 at the offset gap $D_g$ of 3 μm.

The substrate 100 is made of an undoped silicon wafer having a high-resistivity higher than 10,000 Ω·cm. In addition, the silicon wafer has a crystal orientation of <100>, thereby providing transparency in the THz spectra. The central resonator 200 is made of titanium (Ti), and the first 310 and second 360 curved resonators are made of iron (Fe), thereby providing the central resonator and the curved resonator made of different materials.

Referring to FIGS. 1(c) and 1(d), a plasmonic resonator system 20 includes a plurality of plasmonic resonator unit cells 10. The plurality of plasmonic resonator unit cells 10 are formed on the same substrate 100 as an array.

Figures 2A, 2B:
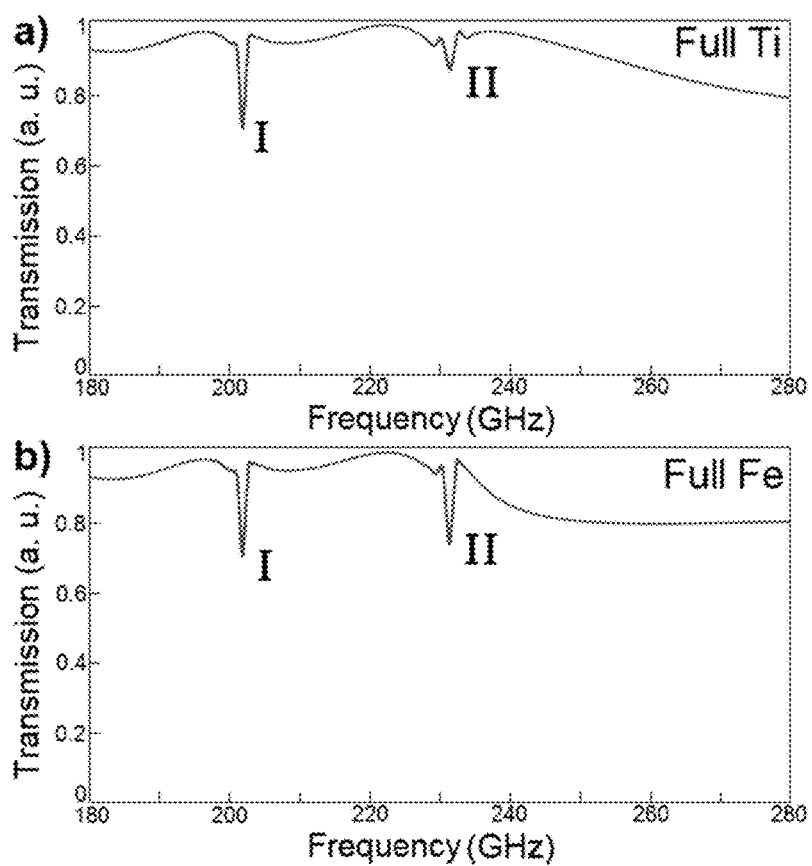
FIG. 2(a) shows a spectral response of a plasmonic resonator unit cell made of Ti according to an embodiment of the subject invention.
FIG. 2(b) shows a spectral response of a plasmonic resonator unit cell made of Fe according to an embodiment of the subject invention.

FIGS. 2(a) and 2(b) show spectral responses of the plasmonic resonator unit cell made of fully Ti and Fe, respectively. Referring to FIGS. 2(a) and 2(b), the plasmonic resonator unit cell shows the differences between the spectral responses of different metallic compositions of the plasmonic resonator unit cell. Referring to FIG. 2(a), due to the poor magnetic moment of the employed metal, it is observed a dramatic decay in the quality of both toroid (I) and magnetic (II) moments compared to the multi-metallic regime. On the other hand, for the full Fe unit cell of FIG. 2(b), the toroidal moment is decayed and the magnetic mode remains unchanged. Such a difference in the magnetic moment (II) reveals the effect of properties of metallic components. For the toroidal moment, the induced magnetic currents are comparable for both full Ti and Fe unit cells. This is because of the absence of the required mismatch between arising magnetic and electric moments from central and peripheral unit cells. In this regime, the magnetic moment of full Ti (Fe) unit cell is considerably weak (strong) and leads to formation of a moderate current density around the central block. For the entirely Fe plasmonic structures, the strong magnetic moment arising from both central and peripheral components gives rise to formation of destructive interferences between modes, reducing the quality of the head-to-tail toroidal moment.

FIGS. 3(a) and 3(b) show a 3D schematic of a magnetic resonance and a 3D schematic of a toroidal resonance around a plasmonic resonator unit cell according to an embodiment of the subject invention, respectively. FIGS. 3(c)-3(e) show electromagnetic responses of a plasmonic resonator unit cell according to an offset gap. FIGS. 3(c)(i)-3(e)(i) show normalized transmission amplitude profiles for the unit cells having different offset gaps, FIGS. 3(c)(ii)-3(e)(ii) show SEM images for the unit cells having different offset gaps, and FIGS. 3(c)(iii)-3(e)(iii) show numerically calculated transmission spectra for the unit cells having different offset gaps.

Referring to the magnetic resonance (m) direction in the upper and lower parts of the magnetic split resonators and central block of FIG. 3(a), strong magnetic fields oscillate in antiphase regime, while the excited weaker magnetic modes at the central resonator act as an in-phase component. On the other hand, FIG. 3(b) illustrates formation of a head-to-tail configuration of the magnetic moments leading to a toroidal dipolar moment (T) at the center of the unit cell created by the currents (j) on the surface of a torus along the circular meridian. The arrows show the current flux direction and magnetic moment (m) oscillation as a close-loop arrangement inside the profile. The head-to-tail configuration is performed with 90° angle to the central block due to antisymmetric geometry of the unit cell.

The corresponding transmitted magnetic radiation from the magnetoplasmonic unit cells arrays can be obtained by taking the summation of the scattered magnetic and incident electromagnetic fields. The total contribution of the far-field scattering of the magnetic field (Hscat) can be written as:

$$H_{scat} = \frac{k^2}{Z_0 4\pi\varepsilon_0}[([(n \times m_c) \times n + ikn \times T_c \times n])] \times n \quad (1)$$

where, k is the wave vector, $Z_0$ is the impedance of the medium, $\varepsilon_0$ is the permittivity of the vacuum, n is a unit vector in the direction of the incident illumination, and finally, $m_c$ and $T_c$ are the magnetic and toroidal dipolar moments, respectively, defined as:

$$\begin{cases} m_c = \frac{1}{2c}\int (r \times J)d^3r \\ T_c = \frac{1}{10c}\int [(r \times J)r - 2r^2 J]d^3r \end{cases} \quad (2)$$

where, J is the induced current density over the entire volume of the area and c is the conventional speed of the light.

To show the strong dependence of the magnetic response to the geometrical parameters, FIGS. 3(c)(i)-3(e)(i) show the effect of the offset gaps between the peripheral and central resonators on the electromagnetic response. Referring to FIGS. 3(c)(i)-3(c)(iii), a sharp magnetic dipolar minimum is observed at ~230 GHz in the experimentally measured normalized transmission amplitude profile for $D_g$=3 μm which is attributed to an in-phase magnetic mode, and, an ultrasharp and distinct line shape is induced at ~203 GHz correlating with the magnetic toroidal dipole (T). At this point, the induced magnetic fields in the satellite split resonators and the close-loop magnetic moment at the offset gap area (the point that both resonators meet each other) cause to formation of a head-to-tail configuration of the magnetic dipoles via suppression of the classical modes in a similar fashion that has been reported for 3D structures.

Tailored plasmonic unit cells of embodiments of the subject invention can have an exquisite geometrical asymmetry that is enhanced by using two different materials. Presence of Fe resonators with high magnetic moment and plasmonic properties helps to formation of giant magnetic current around the middle Ti rectangle. The good electric and poor magnetic responses of the central Ti block help to prevent destructive interference of the strong magnetic moments arising from peripheral magnetic resonators with the moments from the middle rectangle. As a result, formation of a closed-loop head-to-tail magnetic moment configuration would be possible around the central part of the unit cell. Furthermore, the presence of the substrate below the planar unit cell resonator increases the asymetry of the entire metasurface. In this regime, formation of multipolar magnetic and electric modes is feasible, however, these modes are not resonant at the toroidal frequency and cannot be observed in the transmission spectrum. Referring to FIGS. 3(c)(i)-3(e)(i), the increasing the gap distance between the proximal resonators to 4 μm and 5 μm homogenously, shows a trivial broadening in the linewidth and suppression of the toroidal dip which dramatically affects the Q-factor of both magnetic and toroidal modes. For larger offset gaps ($D_g$>4 the excited magnetic field which contributes to formation of the circulating current becomes weaker, causing a huge mismatch between the induced electromagnetic currents in the peripheral and central resonators. The SEM images for the gap spot variations between Fe and Ti resonators in unit cells are shown in FIGS. 3(c)(ii)-3(e)(ii). The experimentally obtained results of FIGS. 3(c)(i)-3(e)(i) are in perfect agreement with the calculated predictions of FIGS. 3(c)(iii)-3(e)(iii). The corresponding experimental Q-factors are as high as=98 and=107 for the magnetic and toroidal modes, respectively, when using the highest peak and lowest minimum of the induced toroidal dipolar dip. Achieving such a high Q-factor by a planar metasurface is the direct result of the strong magnetic resonance confinement and weak free-space coupling.

Figure 4C:
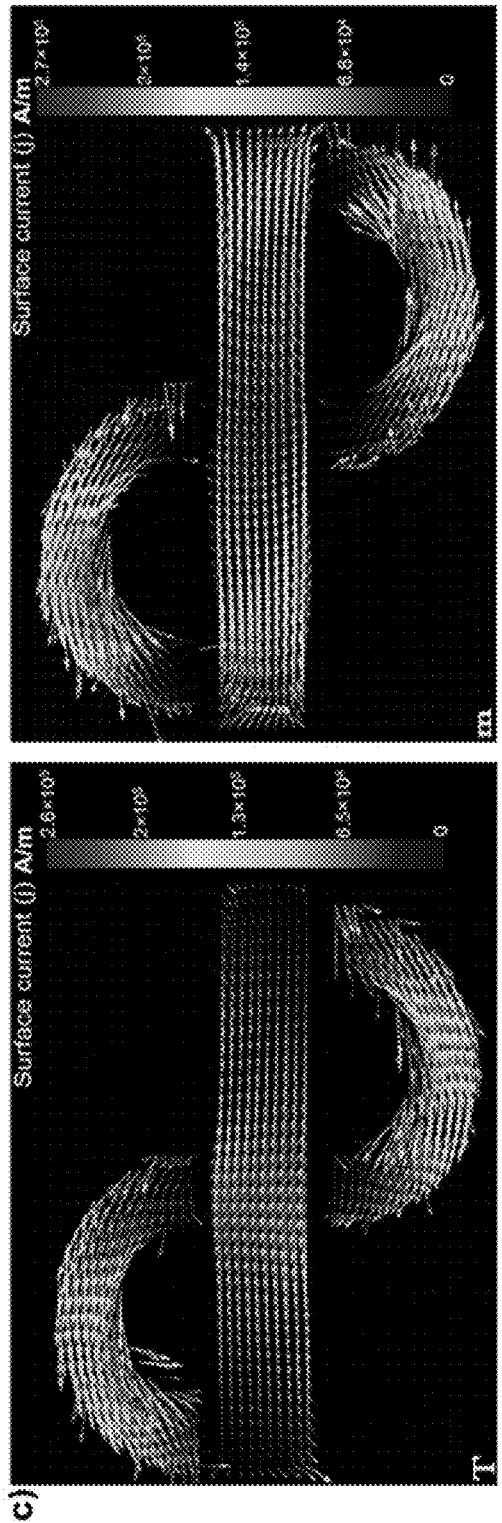
FIG. 4(c) shows surface currents (j) of a plasmonic resonator unit cell at toroidal and magnetic resonances.

FIGS. 4(a) and 4(b) show the numerically calculated local magnetic field (|H|) localization in a standalone unit cell resonator, showing the intense magnetic field confinement at the center of the antenna at the toroidal and magnetic frequencies, respectively in both linear and logarithmic scales. FIGS. 4(a)(iii) and 4(b)(iii) show the cross-sectional panels for the magnetic field (H-field) excitation across the plasmonic unit cell at both toroidal and magnetic resonant moments, respectively. These planes provide a better view of the magnetic field disturbance due to formation of heat-to-tail circular magnetic fields at the center of the unit cell. FIG. 4(c) shows the surface current (j) for both resonant modes.

Figures 5A, 5B, 5C:
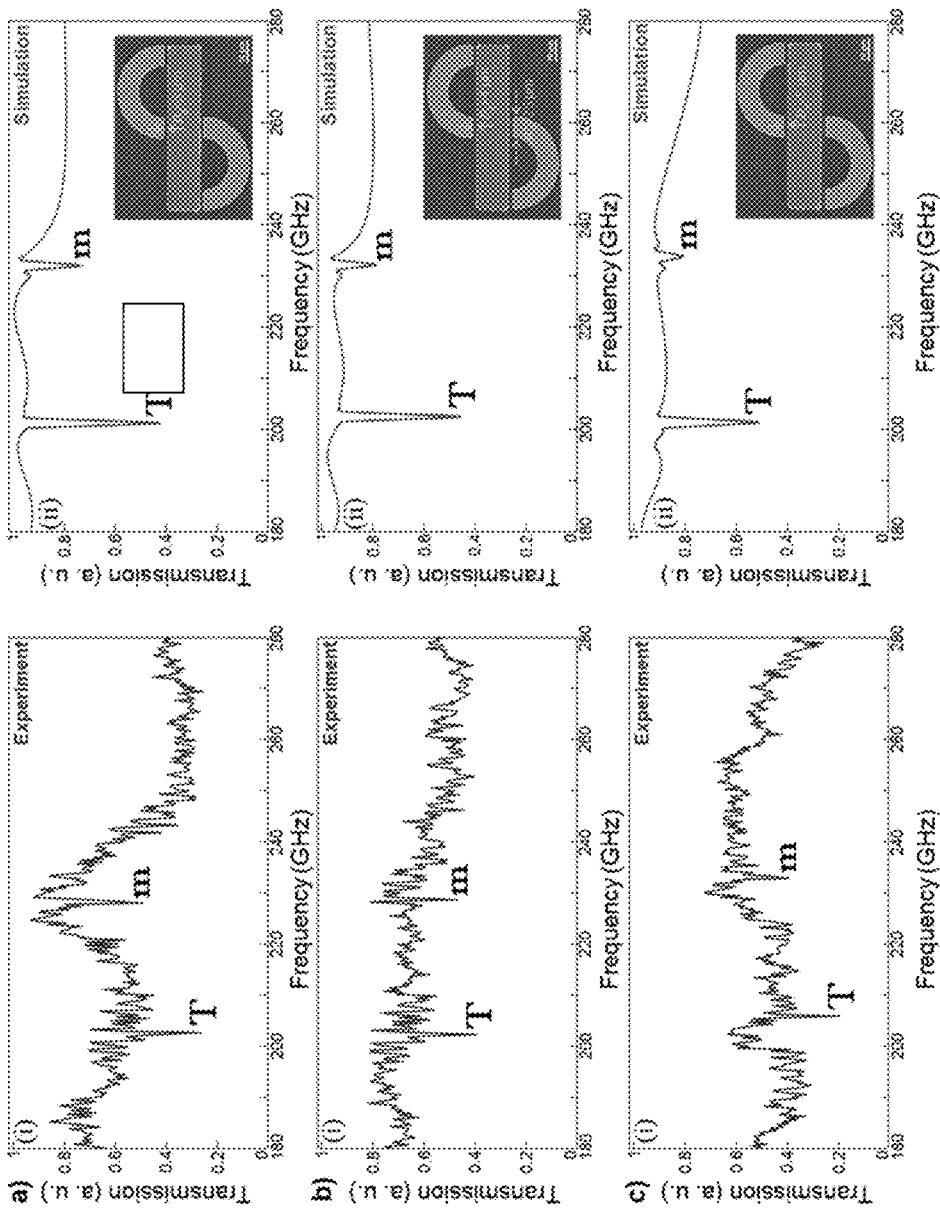
FIG. 5(a) shows an experimental normalized transmission amplitude profile and a numerical normalized transmission amplitude profile of a plasmonic resonator unit cell with $D_g$=3 µm.
FIG. 5(b) shows an experimental normalized transmission amplitude profile and a numerical normalized transmission amplitude profile of a plasmonic resonator unit cell with $D_g$=4 µm.
FIG. 5(c) shows an experimental normalized transmission amplitude profile and a numerical normalized transmission amplitude profile of a plasmonic resonator unit cell with $D_g$=5 µm.

FIGS. 5(a)-5(c) show an experimental normalized transmission amplitude profile and a numerical normalized transmission amplitude profile of plasmonic resonator unit cells with $D_g$=3 μm, 4 μm, and 5 μm. The insets are SEM images according to geometrical parameters. FIG. 5(a)-5(c) show the effect of the geometrical variations in the magnetic peripheral curved resonators on the plasmonic response of the metasurface. In the embodiments of FIGS. 5(a)-5(c), by keeping the width of the central block fixed at $W_2$=40 μm, the plasmonic resonator unit cell reduces the widths of the satellite resonators to $W_1$=25 μm with the radii fixed to R=50 μm. Referring to FIG. 5(a)-5(c), with the reducing width of the magnetic components, strength of the magnetic dipole moment (m) decays dramatically and does not radiate as strong as it does in the previous cases. Therefore, a significant decay is expected in the oscillating magnetic field around the central block (toroidal mode) due to dominant behavior of the excited classical electric dipolar and multi-polar moments. It is noted that despite of possessing prevailing response, both electric and magnetic multipolar moments are not still resonant in this frequency due to poor scattering efficiency. Comparing FIG. 5(a) and FIG. 3(a), the significant decay in the corresponding Q-factor of the toroidal mode is clear. In the same way, the magnetic dipole moment also decays dramatically due to both electric and magnetic classical multipolar modes' dominancy. In this limit, increasing the gap distance between the central and peripheral resonators gives rise to continuing decay in the quality factor of both induced modes (see also e.g., FIGS. 5(b) and 5(c)). For $D_g$=5 μm, the magnetic dipolar moment almost disappears and it is hard to identify the magnetic dipolar moment in the experiments. The minor blue-shift in the positions of both resonant dips is attributed to the geometrical variations, which can be described by Mie scattering theory.

The unique geometry of the multi-metallic resonators of embodiments of the subject invention allows for highly sensitive polarization dependency to the angle of the incident beam. This feature allows for use of the structure of the embodiment as a THz switch. FIGS. 6(a)-6(e) show the polarization dependency of the plasmonic resonator.

Figure 6A:
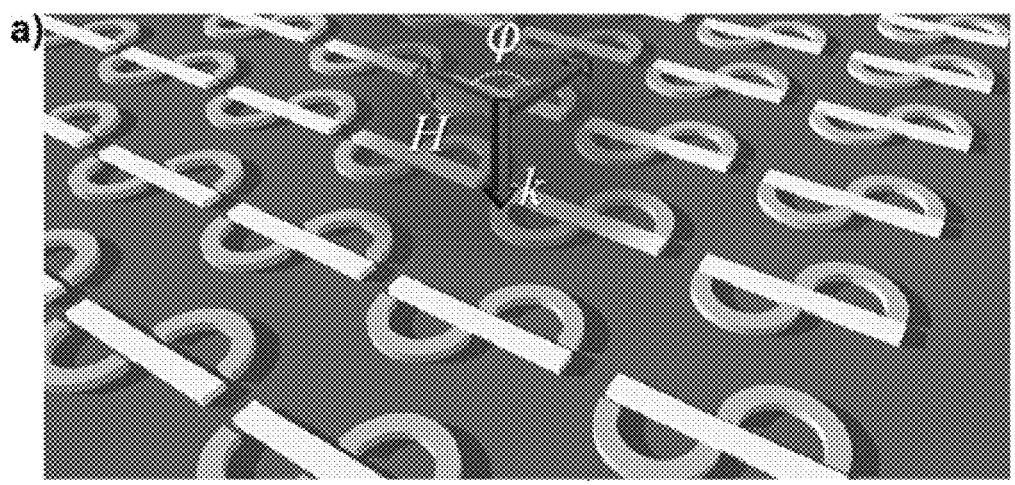
FIG. 6(a) shows a perspective view of a metasurface comprising an array of compositional micro-complex unit cells according to the subject invention.
Figure 6B:
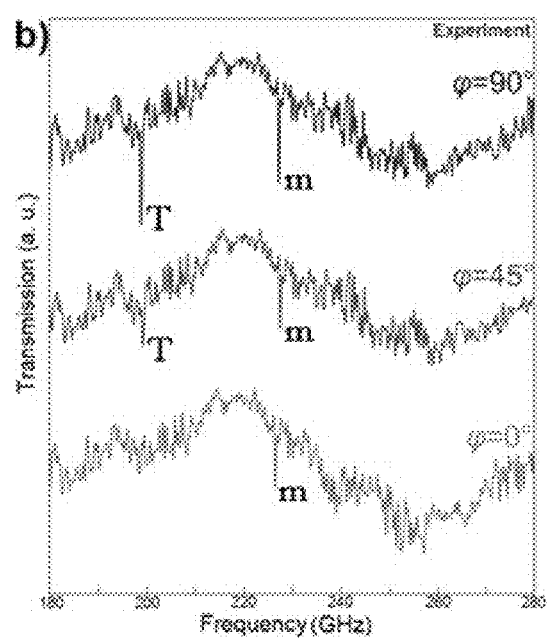
FIG. 6(b) shows normalized transmission amplitude for both toroidal and magnetic responses of a plasmonic resonator unit cell under different magnetic polarization angles.
Figure 6C:
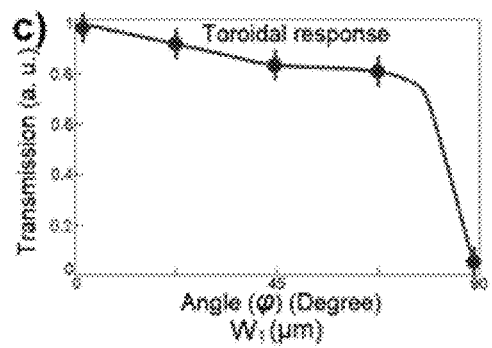
FIG. 6(c) shows a toroidal response of a plasmonic resonator unit cell as a function of incident THz radiation magnetic component angle.
Figure 6D:
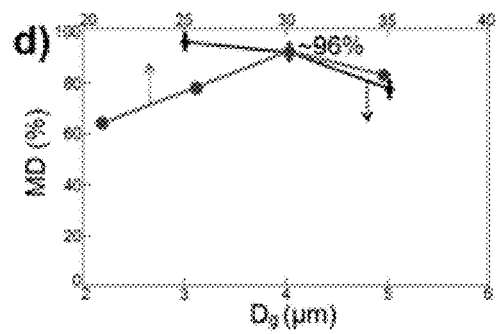
FIG. 6(d) shows modulation depth (MD) percentage as a function of both $W_1$ and $D_g$ of a plasmonic resonator unit cell.
Figure 6E:
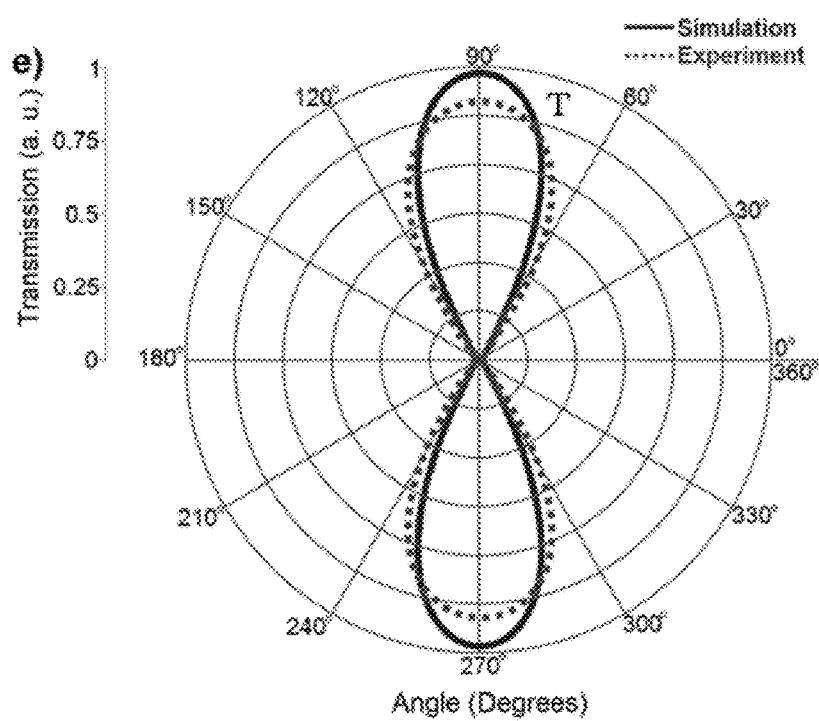
FIG. 6(e) shows a polar plot for experimental and calculated transmission spectra at the position of the toroidal mode.

FIG. 6(a) shows a perspective view of a metasurface comprising arrays of compositional micro-complex unit cells according to embodiments of the subject invention. FIG. 6(b) shows normalized transmission amplitude for both toroidal and magnetic responses of the plasmonic resonator unit cell under different magnetic polarization angles. FIG. 6(c) shows a toroidal response of the plasmonic resonator unit cell as a function of incident THz radiation magnetic component angle, and FIG. 6(d) shows modulation depth (MD) percentage as a function of both $W_1$ and $D_g$ of the plasmonic resonator unit cell. FIG. 6(e) shows a polar plot for experimental and calculated transmission spectra at the position of the toroidal mode.

While the induced toroidal moment by a planar resonator system provides an excellent Q-factor advantage, FIGS. 6(a)-6(e) show the polarization dependency of the provided unit cell. Using the inherent and exotic antisymmetry of the plasmonic resonator unit cell, an efficient polarization-dependent plasmonic toroid switch can be realized. By choosing the best response from the previously provided structures with the highest Q-factor, the behaviour of a sample unit cell is analysed under incident THz beam polarization variations. FIG. 6(a) shows a schematic of the metasurface and the angle (φ) and direction of the incident magnetic field (H). FIG. 6(b) shows the experimentally measured normalized transmission spectra for a unit cell with the following geometrical parameters: $D_g$=3 μm, with L=240 μm, R=50 μm, $W_1$=30 μm, and $W_2$=40 μm, to achieve the highest possible Q-factor.

Referring to FIGS. 6(a) and 6(b), for the incident magnetic beam in the longitudinal polarization limit)(φ=90° parallel to the central block (H||), the same toroidal dipolar dip is induced with high-Q around 0.2 THz and the beam transmissivity is extremely low. Rotating the angle of the polarization to φ=45°, a drastic decay is shown in the toroidal resonant mode dip. Eventually, for φ=0°, where the incident magnetic component entirely transverse ($H^⊥$) to the central block, the toroidal dip is eliminated and the plasmonic metasurface acts as a transparent media at this frequency. As a result, the toroidal resonance characteristics disappear. For φ=0°, due to the antisymmetric geometry of the plasmonic resonator unit cell, the incident electric field component becomes parallel (E∥) to the central block and offset gaps. In this regime, the electric field becomes dominant and the required head-to-tail magnetic moment closed-loop cannot be formed around the central block of the microstructure. However, a distinct magnetic dipolar moment around ~0.23 THz remains due to excitation of the dipolar magnetic resonances by the magnetic peripheral curves via transverse incident magnetic beam. The Q-factor of the induced magnetic dipolar moment in this regime is poorer than the ones in the previous regimes. Moreover, the transmission spectra (for the toroidal response) as a function of the magnetic component of the incident beam angle (φ) is plotted in FIG. 6(c). Such a strong dependence of toroidal minimum can be exploited for fast and efficient on/off routing and filtering purposes.

FIG. 6(e) shows the corresponding modulation-depth (MD) as a key parameter for the metasurface as a function of microstructure's geometries. Referring to FIG. 6(e), the best MD is determined as ~96% for a resonator with the gap size of 3 μm and curved resonator width of 30 μm. The plotted diagram shows the strong dependency of the toroidal dipolar mode and subsequently MD on both geometrical and polarization. Ultimately, the transmission spectra vs polarization angle in polar plane for the provided unit cell can be shown in FIG. 6(d). The obtained experimental and numerical data confirms the strong dependency of the transmissivity of the beam to its polarization direction. The unique electromagnetic response of the provided THz structure can be used to tailor highly sensitive and accurate plasmonic sensor. To this end, it is prepared series of chips with the best Q-factor (with the following geometrical parameters: $D_g$=3 μm, L=240 μm, R=50 $W_1$=30 μm, and $W_2$=40 μm) to achieve precise sensing. The immunosensing samples were prepared in three different configurations: 1) with antibody, 2) with antibody and bovine serum albumin (BSA), and 3) with antibody, bovine serum albumin (BSA), and variant concentration (1 pg/mL to 104 pg/mL) of immobilized ZIKV envelope protein.

Figure 7A:
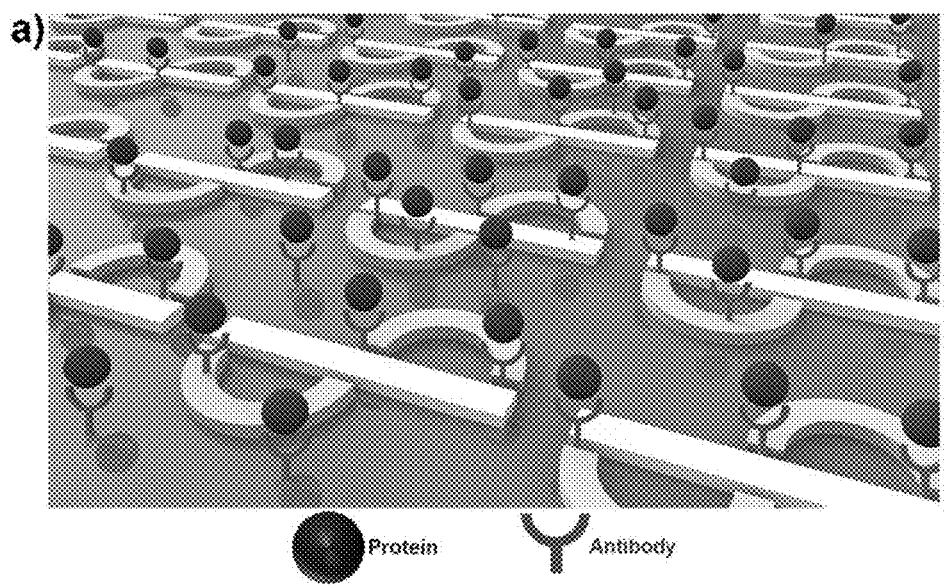
FIG. 7(a) shows an immunosensor according to an embodiment of the subject invention.
Figure 7B:
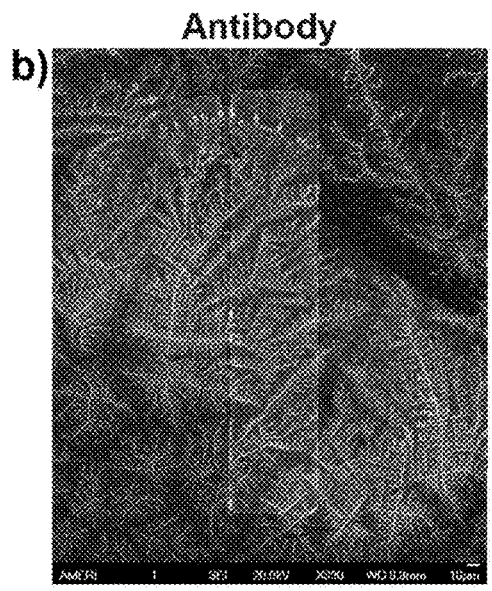
FIG. 7(b) shows an SEM image of an immunosensor covered with antibody according to an embodiment of the subject invention.
Figure 7C:
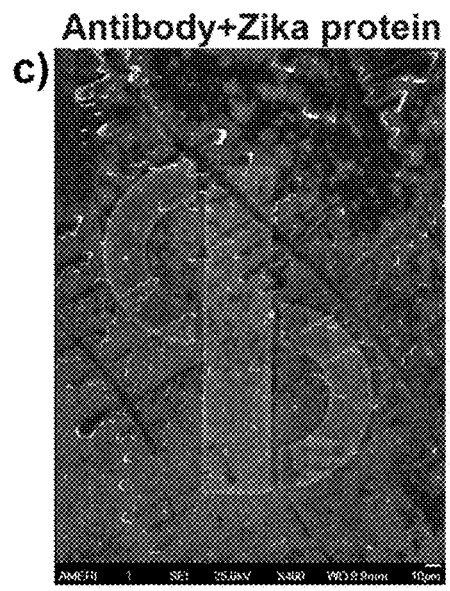
FIG. 7(c) shows an SEM image of an immunosensor covered with ZIKV proteins according to an embodiment of the subject invention.

FIG. 7(a) shows an immunosensor according to an embodiment of the subject invention. FIGS. 7(b) and 7(c) show a SEM image of an immunosensor covered with antibody and ZIKV proteins, respectively. In particular, FIG. 7(a) shows an artistic picture for the metasurface with the presence of antibody and trapped ZIKV proteins around and on the plasmonic resonators, and FIGS. 7(b) and 7(c) show the SEM images of the presence of immobilized ZIKV antibody on a sample metallic microstructure and a chip covered with antibody-attached ZIKV envelope protein, respectively.

Figure 8:
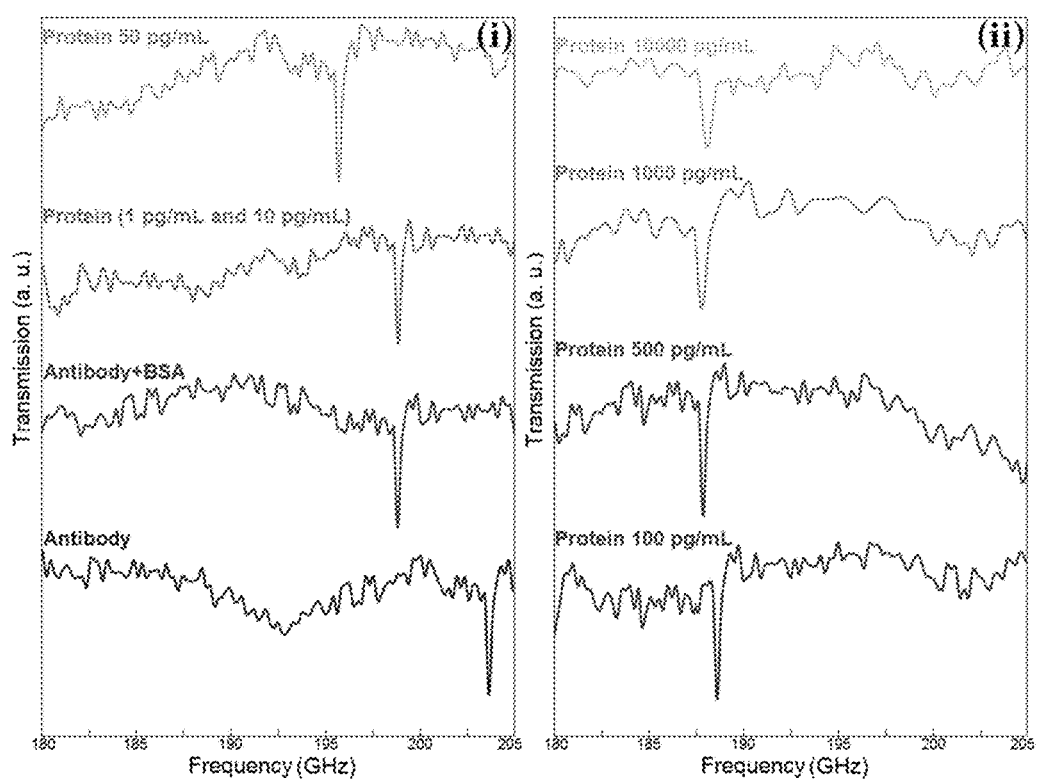
FIG. 8 shows transmission spectra for the toroidal resonant mode behavior for presence of different concentration of ZIKV protein.

FIG. 8 shows the transmission spectra of the plasmonic metasurface for different concentrations of ZIKV envelope protein captured by the antibody. Referring to the behavior of magnetic toroidal mode of FIG. 8, it is observed a prominent resonance in the presence of ZIKV protein concentration between 1 pg/mL to $10^4$ pg/mL. In the earlier embodiment, it is observed excitation of the toroidal resonance mode at 203 GHz for the bare plasmonic resonators. In the presence of the ZIKV antibody, the toroidal mode remained unchanged at 203 GHz due to its optically non-responsiveness to the incident radiation. For the solution comprising ZIKV antibody plus BSA, the magnetic toroid moment is red-shifted to 198 GHz. This is because of formation of a layer on top of the plasmonic sensing device, which affects the entire refractive index of the surrounding ambience and shifting the toroid moment. It is underlined that the presence of BSA layer helps to improve ZIKV protein capturing by respective antibody effectively and preventing non-specific binding of ZIKV envelope protein.

Adding 1 pg/mL and 10 pg/mL of the target protein does not cause any shift in the position of the toroidal moment and it remains at 198 GHz. However, increasing the concentration to 50 pg/mL and 100 pg/mL, the toroidal resonance is shifted to 194 GHz and 188 GHz, respectively. Such a large shift in the resonance frequency shows the sensitivity of the toroid dip to the concentration of the infection protein. However, the narrowness and sharpness of the dipolar toroidal moment is almost unchanged, which helps keeping the sensing precision high by keeping the Q-factor high. This is unusual compared to classical plasmonic biosensing systems operating based on antisymmetric resonant lineshapes such as Fano and EIT resonances where perturbation in the environmental refractive index or physical changes cause to destructive effects on the line shape quality. Such a decay in the quality of resonant modes is caused by their strong dependency on the morphological and geometrical perturbations affecting the spectral response dramatically.

Further increase in the concentration of ZIKV envelope protein to 500 pg/mL leads to a shift of the position of the pronounced toroidal resonant dip to 187 GHz. In continue, by increasing the concentration of target protein to $10^3$ pg/mL and $10^4$ pg/mL, it is observed a drastic decay in the quality of toroidal mode in both cases.

Figures 9A, 9B:
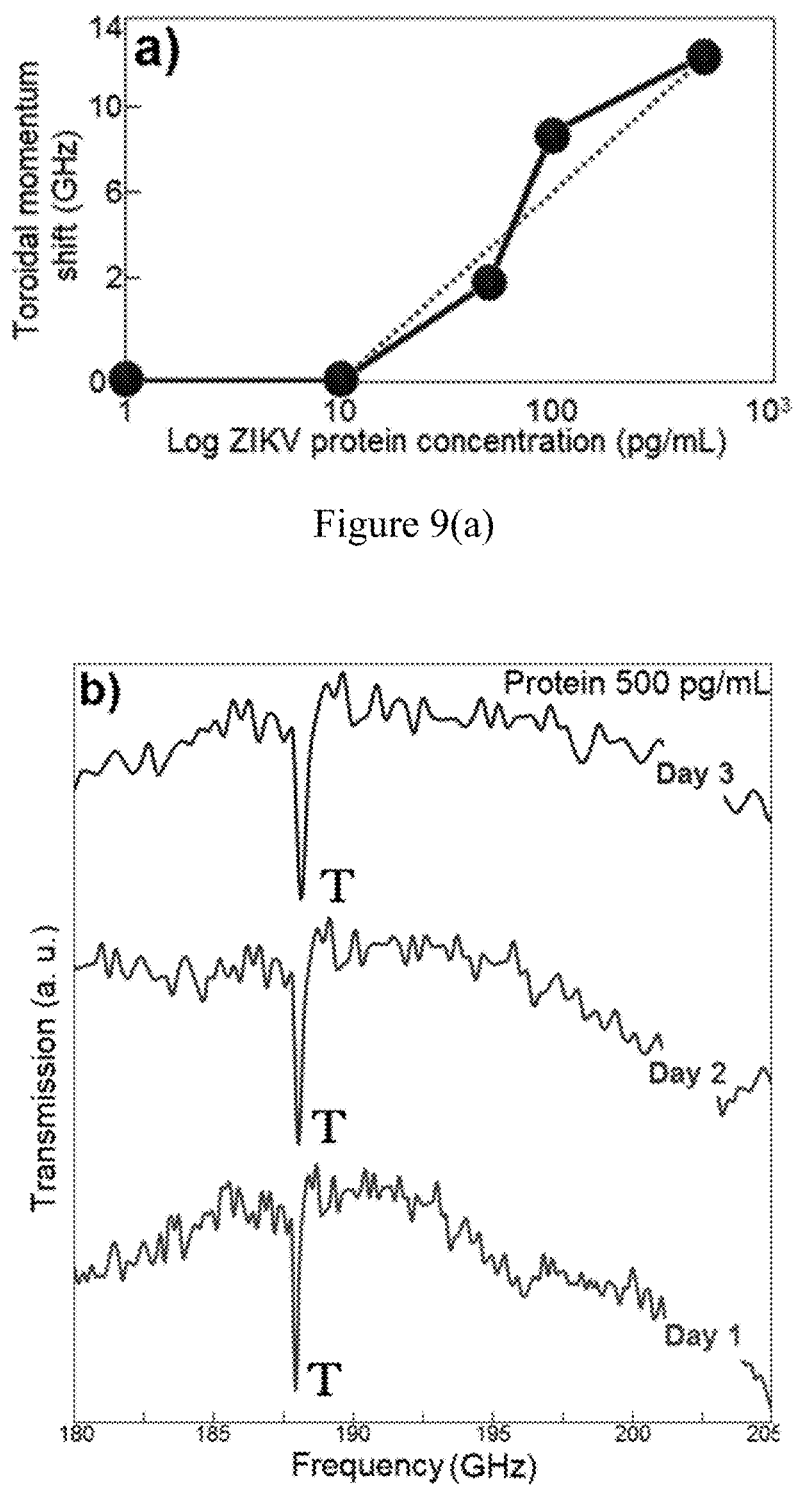

FIG. 9(a) shows the frequency shifts (GHz) as a function of protein concentration (pg/mL). Referring to FIG. 9(a), ZIKV protein with the concentration ranging from 1 pg/mL to 10 pg/mL does not cause to a noticeable frequency shift, reflecting weak sensitivity. While for the concentration ranging from 50 pg/mL to 500 pg/mL a significant red-shift in the frequency of the toroidal mode is recorded. The limit of detection (LOD) can be defined by: LOD=3(SD)/S, where "SD" is the standard deviation of the frequency shift and "S" is the slope of the fitting line (shown by the dashed line in FIG. 9(a)), and the LOD is quantified as ~24 pg/mL. By defining the slope of the toroidal position shift as a function of ZIKV envelope protein concentration, it is estimated the sensitivity of the structure as 6.47 GHz/log(pg/mL).

FIG. 9(b) shows the longevity and repeatability of the provided THz plasmonic biosensors. The samples with the antibody are prepared with the described technique in below EXAMPLE and stored at 4° C. before the measurements. Referring to FIG. 9(b), the transmission spectra are measured for three consecutive days with the ZIKV concentration of 500 pg/mL, and the resonance quality remains excellent for three days. However, after this period of time, the toroidal dip becomes broader and dramatically damps. This deterioration also includes a significant blue-shift in the position of magnetic resonant mode to the higher energies. That is, the ability to identify low concentrations of a specific biomarker with low molecular weight will be feasible by using the proposed metasensor.

Embodiments of the subject invention show excitation of ultrasharp toroidal and magnetic dipoles in THz frequencies using bi-metallic asymmetrical planar resonators. Using the magnetic nature of Fe and also the exotic geometrical design of the proposed structure, the embodiments provide experimentally measured Q factor of $10^7$ for the toroidal resonance. Taking advantage of the high-Q toroidal moment resonance, the embodiments also provide biosensing capability of the proposed structures. Spectral response of the samples loaded with the relevant antibody to the assays of ZIKV envelope protein with different concentrations shows that limit of detection of ~24 pg/mL and 6.47 GHz/log(pg/ mL) is achievable. Further, the embodiments show that the demonstrated biosensing platform could be reliable up to three days. The unique geometry of the plasmonic resonators also results in high polarization sensitivity which allows for their use in THz switching applications.

The subject invention includes, but is not limited to, the following exemplified embodiments.

Embodiment 1

A plasmonic resonator unit cell, comprising:
a central resonator;
a first curved resonator disposed at a first side of the central resonator; and
a second curved resonator disposed at a second side of the central resonator,
the first curved resonator and the second curved resonator being asymmetric to each other with respect to the central resonator.

Embodiment 2

The plasmonic resonator unit cell according to embodiment 1, the second side being an opposite side of the first side with respect to the central resonator.

Embodiment 3

The plasmonic resonator unit cell according to any of embodiments 1-2, the central resonator being made of titanium (Ti) and the first and second curved resonators being made of iron (Fe).

Embodiment 4

The plasmonic resonator unit cell according to any of embodiments 1-3, the central resonator having a rectangular shape and each of the first and second curved resonators having a circular shape.

Embodiment 5

The plasmonic resonator unit cell according to any of embodiments 1-4, a first end of the first curved resonator corresponding to a first longitudinal end of the central resonator, a second end of the first curved resonator corresponding to a center of the central resonator, a first end of the second curved resonator corresponding to the center of the central resonator, and a second end of the second curved resonator corresponding to a second longitudinal end of the central resonator.

Embodiment 6

The plasmonic resonator unit cell according to any of embodiments 1-5, further comprising a silicon substrate; the central resonator, the first curved resonator, and the second curved resonator being disposed on the silicon substrate.

Embodiment 7

The plasmonic resonator unit cell according to embodiment 6, the silicon substrate having a resistivity higher than 10,000 $\Omega \cdot cm$ and having a crystal orientation of <100>.

Embodiment 8

The plasmonic resonator unit cell according to any of embodiments 1-7, further comprising an oxide layer on the first and second curved resonators.

Embodiment 9

A plasmonic resonator system, comprising the plurality of plasmonic resonator unit cells according to any of embodiments 1-8.

Embodiment 10

An immunosensor, comprising: the plasmonic resonator unit cell according to any of embodiments 1-9; and an antibody disposed on the plasmonic resonator unit cell.

Embodiment 11

A plasmonic resonator, comprising:
a substrate;
a central resonator on the substrate;
a first curved resonator disposed on the substrate and disposed at a first side of the central resonator; and
a second curved resonator disposed on the substrate and disposed at a second side of the central resonator,
the first curved resonator and the second curved resonator being asymmetric to each other with respect to the central resonator, and
the central resonator and at least one of the first and second curved resonators being made of different materials.

Embodiment 12

The plasmonic resonator according to embodiment 11, the substrate being a silicon substrate, the central resonator being a Ti layer, and each of the first and second curved resonators being a Fe layer.

Embodiment 13

The plasmonic resonator according to any of embodiments 11-12, the central resonator having a rectangular shape and each of the first and second curved resonators having a circular shape.

Embodiment 14

The plasmonic resonator according to any of embodiments 11-13, a first end of the first curved resonator corresponding to a first longitudinal end of the central resonator, a second end of the first curved resonator corresponding to a center of the central resonator, a first end of the second curved resonator corresponding to the center of the central resonator, and a second end of the second curved resonator corresponding to a second longitudinal end of the central resonator.

Embodiment 15

The plasmonic resonator according to embodiment 14, each of the second end of the first curved resonator and the first end of the second curved resonator being spaced apart from the central resonator by an offset gap.

Embodiment 16

The plasmonic resonator according to any of embodiments 14-15, the first longitudinal end and the second longitudinal end being disposed at opposite sides with respect to the center of the central resonator.

Embodiment 17

The plasmonic resonator according to any of embodiments 12-16, the silicon substrate being an undoped silicon wafer.

Embodiment 18

The plasmonic resonator according to any of embodiments 12-17, the Fe layer including an oxide layer.

Embodiment 19

A plasmonic resonator system, comprising:
a silicon substrate having a crystal orientation of <100>; and
a plurality of plasmonic resonators on the silicon substrate,
each of the plurality of plasmonic resonators comprising:
a Ti rectangular central resonator on the silicon substrate;
a first Fe curved resonator disposed on the silicon substrate and disposed at a first side of the Ti rectangular central resonator; and
a second Fe curved resonator disposed on the silicon substrate and disposed at a second side of the Ti rectangular central resonator,
a first end of the first Fe curved resonator corresponding to a first longitudinal end of the Ti rectangular central resonator, a second end of the first Fe curved resonator corresponding to a center of the Ti rectangular central resonator, a first end of the second Fe curved resonator corresponding to the center of the Ti rectangular central resonator, and a second end of the second Fe curved resonator corresponding to a second longitudinal end of the Ti rectangular central resonator, and
each of the second end of the first Fe curved resonator and the first end of the second Fe curved resonator being spaced apart from the Ti rectangular central resonator by an offset gap.

Embodiment 20

An immunosensor, comprising:
the plasmonic resonator system according to embodiment 19; and
an antibody disposed on the plasmonic resonator system.

Embodiment 21

A method of manufacturing a plasmonic resonator unit cell, the method comprising:
preparing a silicon wafer;
patterning a photoresist on the silicon wafer;
depositing a titanium (Ti) layer over the silicon wafer;
depositing an iron (Fe) layer over the silicon wafer; and
removing the patterned photoresist,
the patterned photoresist including a central resonator part for the Ti layer, and a first curved resonator part and a second curved resonator part for the Fe layer,
the first curved resonator part being located at a first side of the central resonator part,
the second curved resonator part being located at a second side of the central resonator part, and
the first curved resonator part and the second curved resonator part being asymmetric to each other with respect to the central resonator part.

Embodiment 22

The method according to embodiment 21, further comprising sonicating the silicon wafer in acetone, rinsing the silicon wafer with isopropyl alcohol (IPA) and deionized (DI) water, and drying the silicon wafer by Nitrogen before the patterning.

Embodiment 23

The method according to any of embodiments 21-22, further comprising plunging the silicon wafer in remover PG after removing the patterned photoresist.

Embodiment 24

The method according to any of embodiments 21-23, the silicon wafer being an undoped silicon wafer, having a resistivity higher than 10,000 $\Omega \cdot cm$, and having a crystal orientation of <100>.

Embodiment 25

The method according to any of embodiments 21-24, the depositing the Ti layer being performed by e-beam evaporation.

Embodiment 26

The method according to any of embodiments 21-25, the depositing the Fe layer being performed by e-beam evaporation.

Embodiment 27

The method according to any of embodiments 21-26, the photoresist being a negative photoresist.

Embodiment 28

A method of testing a virus, comprising:
preparing the plasmonic resonator unit cell of any of embodiments 21-27;
forming antibody on the plasmonic resonator unit cell; and
incubating the antibody-modified plasmonic resonator unit cell in a phosphate buffer solution (PBS).

Embodiment 29

The method according to embodiment 28, further comprising incubating the antibody-modified plasmonic resonator unit cell in a solution of a recombinant Zika.

A greater understanding of the present invention and of its many advantages may be had from the following example, given by way of illustration. The following example is illustrative of some of the methods, applications, embodiments, and variants of the present invention. It is, of course, not to be considered as limiting the invention. Numerous changes and modifications can be made with respect to the invention.

Example 1

For the fabrication of the embodiments of the subject invention, a two-level lithography based microfabrication process is developed. An undoped and high-resistivity silicon wafer (>10,000 Ω·cm) with the crystal orientation of <100> is used as a substrate to provide the required transparency in the THz spectra. It is sonicated in acetone for 10 min, and rinsed with isopropyl alcohol (IPA) and deionized (DI) water, and dried by Nitrogen prior to the fabrication process. In continue, a negative photoresists (NLOF 2020) is deposited and then patterned intently in two different steps. By employing e-beam evaporation, 300 nm of Fe and Ti layers are deposited separately with the rate of 2 Å/s (99.99% purity for Ti and 99.95% purity for Fe, pressure ~5×10-7 Torr). The lift-off process is performed for 15 min by immersing the samples in acetone. Finally, the samples are plunged in remover PG for 120 min at 70° C. heat followed by IPA and DI water rinse. The SEM images shown can be obtained using JEOL 6330 tool.

Example 2

To characterize samples and extract the plasmon response of arrays with and without biological targets, a millimeter wave backward wave oscillator (BWO) setup combined with frequency multiplier (Microtech Instruments, Inc.) and broadband pyroelectric detector (Gentec Electro Optics Inc.) is operated at room-temperature. The spectral range of the incident radiation is between 100 GHz and 1.5 THz. The spectral resolution of the system is 10 MHz.

Example 3

Preparation of samples for fingerprint biological assay use both lyophilized 99% bovine serum albumin (BSA) purchased from Sigma-Aldrich, and pH 7.4 phosphate buffer solution (PBS) to dissolve the immunoreagents. For preparing the samples for real-time characterization, 10 μL of Zika antibodies (1 mg/mL) in PBS are locally deposited on the sensing area of THz structures and incubated for 15 min. After washing the chips with PBS, antibody-modified structures are incubated in PBS containing 0.1 wt. % BSA for 15 min, and then, in a solution of a recombinant Zika diluted in PBS for at least 20 min (The ZIKV protein concentration is ranged from 1 to $10^4$ pg/mL). Once prepared, antibody-functionalized microstructures are rinsed and stored at 4° C. until used. The mouse monoclonal antibody for ZIKV protein and the envelope proteins can be purchased from Aalto Bio Reagents and Sino Biological Inc. respectively.

Example 4

Numerical analysis is performed using three-dimensional (3D) finite-difference time-domain (FDTD) method (Lumerical). The bi-metallic resonators on top of a semi-infinite high-resistive silicon substrate are simulated using the refractive index of 3.9 for Si at THz domain. The dielectric responses of the Ti antennas are taken from experimentally defined Palik constants. Perfectly matched layers (PMLs) are used as the boundaries, and the light source is a linear electrical plane wave (with both s- and p-polarized beam) with the pulse length of 150 ps. To achieve high accurate results, the 3D grid sizes in all three axes are set to 25 nm.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Maier, S. A., Brongersma, M. L., Kik, P. G., Meltzer, S., Requicha, A. A. G., & Atwater, H. A. Plasmonics—A route to nanoscale optical devices. Adv. Mater. 13, 1501-1505 (2001).
2. Zayats, A. V., & Maier, S. A. Active plasmonics and tuneable plasmonic metamaterials. (Wiley, Danvers, Mass., 2013).
3. Lindquist, N. C., Nagpal, P., McPeak, K. M., Norris, D. J., & Oh, S. -H. Engineering metallic nanostructures for plasmonics and nanophotonics. Rep. Prog. Phys. 75, 036501 (2012).
4. Zijlstra, P.; Paulo, P. M. R.; & Orrit, M. Optical detection of single non-absorbing molecules using the surface plasmon resonance of a gold nanorod. Nat. Nanotechnol. 7, 379-382 (2012).
5. Anker, J. N.; Hall, W. P.; Lyandres, O.; Shah, N. C.; Zhao, J.; and Van Duyne, R. P. Biosensing with plasmonic nanosensors. Nat. Mater. 7, 442-453 (2008).
6. Dondapati, S. K.; Sau, T. K.; Hrelescu, C.; Klar, T. A.; Stefani, F. D.; and Feldmann, J. Label-free biosensing based on single gold nanostars as plasmonic transducers. ACS Nano 4, 6318-6322 (2010).
7. Kravets, V. G. et al. Singular phase nano-optics in plasmonic metamaterials for label-free single-molecule detection. Nat. Mater. 12, 304-309 (2013).
8. Wang, N., Hashemi, M. R., & Jarrahi, M. Plasmonic photoconductive detectors for enhanced terahertz detection sensitivity. Opt. Express 21, 17221-17227 (2013).
9. Xu, W. et al. Gold nanoparticle-based terahertz metamaterial sensors: mechanisms and applications. ACS Photonics. 3, 2308-2314 (2016).
10. Wiltshire, M. C. K. et al. Microstructured magnetic materials for RF flux guides in magnetic resonance imaging. Science 291, 849-851 (2001).
11. Lee, H. -J. et al. A planar split-ring resonator-based microwave biosensor for label-free detection of biomolecules. Sensor Actuat. B-Chem. 169, 26-31 (2012).
12. Fischer, B. M., Walther, M., & Jepsen, P. U. Far-infrared vibrational modes of DNA components studied by terahertz time-domain spectroscopy. Phys. Med. Biol. 47, 3807-3814 (2002).
13. Berrier, A. et al. Selective detection of bacterial layers with terahertz plasmonic antennas. Biomed. Opt. Express 3, 2937-2949 (2012).
14. Menikh, A., MacColl, R., & Mannella, C. A. Terahertz biosensing technology: Frontiers and progress. Chem. Phys. Chem. 3, 655-658 (2002).
15. Park, S. J. et al. Detection of microorganisms using terahertz metamaterials. Sci. Rep. 4, 4988 (2014).
16. Smye, S. W., Chamberlain, J. M., Fitzgerald, A. J., & Berry, E. The interaction between terahertz radiation and biological tissue. Phys. Med. Biol. 46, R101-R112 (2001).
17. Ferguson, B., & Zhang, X. -C. Materials for terahertz science and technology. Nat. Mater. 1, 26-33 (2002).
18. Mickan, S. P. et al. Label-free bioaffinity detection using terahertz technology. Phys. Med. Biol. 47, 3789-3795 (2002).

19. Nagel, M., Forst, M., & Kurz, H. THz biosensing devices: fundamentals and technology. J. Phys. Condens. Mat. 18, S601-S618 (2006).
20. Tao, H. et al. Performance enhancement of terahertz metamaterials on ultrathin substrates for sensing applications. Appl. Phys. Lett. 97, 261909 (2010).
21. Wu, C. et al. Fano-resonant asymmetric metamaterials for ultrasensitive spectroscopy and identification of molecular monolayers. Nat. Mater. 11, 69-75 (2012).
22. Ashkin, A., & Dziedzic, J. M. Optical trapping and manipulation of viruses and bacteria. Science 235, 1517 (1987).
23. Kuznetsov, A. I. et al. Laser fabrication of large-scale nanoparticle arrays for sensing applications. ACS Nano 5, 4843-4849 (2011).
24. Musso, D. et al. Detection of Zika virus in saliva. J. Clin. Virol. 68, 53-55 (2015).
25. Saxena, S. K., Elahi, A., Gadugu, S. & Prasad, A. K. Zika virus outbreak: an overview of the experimental therapeutics and treatment. VirusDis. 27, 111 (2016).
26. Vorou, R. Letter to the editor: diagnostic challenges to be considered regarding Zika virus in the context of the presence of the vector *AEDES ALBOPICTUS* in Europe. Eurosurveillance 21, 30161 (2016).
27. Song, J. et al. Instrument-free point-of-care molecular detection of Zika virus. Anal. Chem. 88, 7289-7294 (2016).
28. Kaushik, A. et al. Electrochemical biosensors for early stage Zika diagnostics. Trends Biotechnol. In press (2017). DOI: 10.1016/j.tibtech.2016.10.001
29. Gallinet, B., & Martin, 0. J. F. Influence of electromagnetic interactions on the line shape of plasmonic Fano resonances. ACS Nano 5, 8999-9008 (2011).
30. Singh, R. et al. The Fano resonance in symmetry broken terahertz metamaterials. IEEE T THz Sci. Technol. 3, 820-826 (2013).
31. Yanik, A. A. et al. Seeing protein monolayers with naked eye through plasmonic Fano resonances. Proc. Natl. Acad. Sci. USA 108, 11784-11789 (2011).
32. Wang, J. et al. Double Fano resonances due to interplay of electric and magnetic plasmon modes in planar plasmonic structure with high sensing sensitivity. Opt. Express 21, 2236-2244 (2013).
33. Gu, J. et al. Active control of electromagnetically induced transparency analogue in terahertz metamaterials. Nat. Commun. 3, 1151 (2012).
34. Chang, W. -S. et al. A plasmonic Fano switch. Nano Lett. 12, 4977-4982 (2012).
35. Mario, L. Y., Darmawan, S. & Chin, M. K. Asymmetric Fano resonance and bistability for high extinction ratio, large modulation depth, and low power switching. Opt. Express 14, 12770-12781 (2006).
36. Ott, C. et al. Lorentz meets Fano in spectral lineshapes: A universal phase and its laser control. Science 340, 716-720 (2013).
37. Yu, X., Shi, L., Han, D., Zi, J., Braun, P. V. High quality factor metallodielectric hybrid plasmonic-photonic crystals. Adv. Funct. Mater. 20, 1910-1916 (2010).
38. Cao, W. et al. Low-loss ultra-high-Q dark mode plasmonic Fano metamaterials. Opt. Lett. 37, 3366-3368 (2012).
39. Singh, R. et al. Ultrasensitive terahertz sensing with high-Q Fano resonances in metasurfaces. Appl. Phys. Lett. 105, 171101 (2014).
40. Fedetov, V. A., Rogacheva, A. V., Savinov, V., Tsai, D. P., & Zheludev, N. I. Resonant transparency and non-trivial non-radiating excitation in toroidal metamaterials. Sci. Rep. 3, 2967 (2013).
41. Liu, W., Shi, J., Lei, B., Hu, H., & Miroshnichenko, A. E. Efficient excitation and tuning of toroidal dipoles within individual homogenous nanoparticles. Opt. Express 23, 24738-24747 (2015).
42. Kaelberer, T., Fedotov, V. A., Papasimakis, N., Tsai, D. P.; & Zheludev, N. I. Toroidal dipolar response in a metamaterial. Science 330, 1510-1512 (2010).
43. Gupta, M. et al. Sharp toroidal resonances in planar terahertz metasurfaces. Adv. Mater. 28, 8206-8211 (2016).
44. Gupta, M., & Singh, R. Toroidal versus Fano resonances in high Q planar THz metamaterials. Adv. Opt. Mater. 4, 2119-2125 (2016).
45. Jackson, J. D. Classical Electrodynamics (Wiley, New York, 1999).
46. Papasimakis, N., Fedotov, V. A., Savinov, V., Raybould, T. A., & Zheludev, N. I. Electromagnetic toroidal excitations in matter and free space. Nat. Mater. 15, 263-271 (2016).
47. Afanasiev, G. N., & Dubovik, V. M. Electromagnetic properties of a toroidal solenoid. J. Phys. A 25, 4869-4886 (1992).
48. Dubovik, V. M., & Tugushev, V. V. Toroid moments in electrodynamics and solid-states physics. Phys. Rep. 187, 145-202 (1990).
49. Fan, Y., Wei, Z., Li, H., Chen, H., & Soukoulis, C. M. Low-loss and high-Q planar metamaterial with toroidal moment. Phys. Rev. B 87, 115417 (2013).
50. Savinov, V., Fedotov, V. A., & Zheludev, N. I. Toroidal dipolar excitation and macroscopic electromagnetic properties of metamaterials. Phys Rev. B 89, 205112 (2014).
51. Ye, Q. W., Guo, L. Y., Li, M. H., Liu, Y., Xiao, B. X., & Yang, H. L. The magnetic toroidal dipole in steric metamaterial for permittivity sensor application. Phys. Scr. 88, 055002 (2013).
52. Ordal, M. A., Bell, R. J., Alexander, R. W., Newquist, L. A., & Querry, M. R. Optical properties of Al, Fe, Ti, Ta, W, and Mo at submillimeter wavelengths. Appl. Opt. 27, 1203-1209 (1988).
53. Wu, W., He, Q., & Jiang, C. Magnetic iron oxide nanoparticles: synthesis and surface functionalization strategies. Nanoscale Res. Lett. 3, 397-415 (2008).
54. Palik, E. D. Handbook of optical constants of solids (Academic Press, San Diego, 1997).
55. Newton, R. G. Scattering theory of waves and particles (Springer, New York, 1982).
56. Zhu, W. M. et al. Switchable magnetic metamaterials using micromachining process. Adv. Mater. 23, 1792-1796 (2011).
57. Meng, F. -Y., Wu, Q., Erni, D., Wu, K., & Lee, J. -C. Polarization-independent metamaterial analog of electromagnetically induced transparency for a refractive-index-based sensor. IEEE T. Microw. Theory 60, 3013-3022 (2012).
58. Wu, C. et al. Fano-resonant asymmetric metamaterials for ultrasensitive spectroscopy and identification of molecular monolayers. Nat. Mater. 11, 69-75 (2012).
59. Dong, Z. -G. et al. Enhanced sensing performance by the plasmonic analog of electromagnetically induced transparency in active metamaterials. Appl. Phys. Lett. 97, 114101 (2010).
60. Ahmadivand, A. & Pala, N. Tailoring negative-refractive-index metamaterials composed of semiconductormetal-semiconductor gold ring/disk cavity heptamers to support strong Fano resonances in the visible spectrum. J. Opt. Soc. Am. A 32, 204-212 (2015).
61. Currie, L. A. Detection and quantification limits: origin and historical overview. Anal. Chim. Acta 391, 127-134 (1999).
62. Sinha, R. et al. Tunable room temperature THz sources based on nonlinear mixing in a hybrid optical and THz micro-ring resonator. Sci. Rep. 5, 9422 (2015).
63. Sinha, R. et al. Tunable, room temperature CMOS-compatible THz emitters based on nonlinear mixing in microdisk resonators. J. Infrared Millim. THz Waves 37, 230-242 (2016).
64. Zhang, H., Guo, P., Chan, P., Chang, S., & Yuan, J. Liquid-crystal-filled photonic crystal for terahertz switch and filter. J. Opt. Soc. Am. B 26, 101-106 (2009).
65. Zhang, X. et al. Terahertz filters based on frequency selective surfaces for high-speed terahertz switch. J. Appl. Phys. 113, 014504 (2013).

What is claimed is:

1. A plasmonic resonator unit cell, comprising:
a substrate;
a central resonator disposed on the substrate;
a first curved resonator disposed on the substrate, only at a first side of the central resonator, and being monolithically formed; and
a second curved resonator disposed on the substrate, only at a second side of the central resonator, and being monolithically formed,
the central resonator being a monolithically-formed bar having an upper portion and a lower portion,
the first curved resonator and the second curved resonator being asymmetric to each other with respect to the central resonator,
the first curved resonator facing the upper portion of the central resonator,
the second curved resonator facing the lower portion of the central resonator,
the first side and the second side being different from each other,
a cross-section of the central resonator, taken in a direction parallel to an upper surface of the substrate, being rectangular,
a first end of the first curved resonator being disposed adjacent to a first longitudinal end of the central resonator,
a second end of the first curved resonator being disposed adjacent to a center of the central resonator,
a first end of the second curved resonator being disposed adjacent to the center of the central resonator, and
a second end of the second curved resonator being disposed adjacent to a second longitudinal end of the central resonator.

2. The plasmonic resonator unit cell according to claim 1, the second side being an opposite side of the first side with respect to the central resonator.

3. The plasmonic resonator unit cell according to claim 2, the central resonator being made of titanium (Ti) and the first and second curved resonators being made of iron (Fe).

4. The plasmonic resonator unit cell according to claim 3, each of the first and second curved resonators having a circular shape.

5. The plasmonic resonator unit cell according to claim 4, the substrate being a silicon substrate.

6. The plasmonic resonator unit cell according to claim 5, the silicon substrate having a resistivity higher than 10,000 Ω·cm and having a crystal orientation of <100>.

7. The plasmonic resonator unit cell according to claim 5, further comprising an oxide layer on the first and second curved resonators.

8. A plasmonic resonator system, comprising a plurality of plasmonic resonator unit cells according to claim 5.

9. An immunosensor, comprising:
the plasmonic resonator unit cell according to claim 5; and
an antibody disposed on the plasmonic resonator unit cell.

10. A plasmonic resonator, comprising:
a substrate;
a central resonator on the substrate;
a first curved resonator disposed on the substrate, only at a first side of the central resonator, and being monolithically formed; and
a second curved resonator disposed on the substrate, only at a second side of the central resonator, and being monolithically formed,
the central resonator being a monolithically-formed bar having an upper portion and a lower portion,
the first curved resonator and the second curved resonator being asymmetric to each other with respect to the central resonator,
the first curved resonator facing the upper portion of the central resonator,
the second curved resonator facing the lower portion of the central resonator,
the central resonator and at least one of the first and second curved resonators being made of different materials,
the first side and the second side being different from each other,
a cross-section of the central resonator, taken in a direction parallel to an upper surface of the substrate, being rectangular,
a first end of the first curved resonator being disposed adjacent to a first longitudinal end of the central resonator,
a second end of the first curved resonator being disposed adjacent to a center of the central resonator,
a first end of the second curved resonator being disposed adjacent to the center of the central resonator, and
a second end of the second curved resonator being disposed adjacent to a second longitudinal end of the central resonator.

11. The plasmonic resonator according to claim 10, the substrate being a silicon substrate, the central resonator being a Ti layer, and each of the first and second curved resonators being a Fe layer.

12. The plasmonic resonator according to claim 11, each of the first and second curved resonators having a circular shape.

13. The plasmonic resonator according to claim 10, each of the second end of the first curved resonator and the first end of the second curved resonator being spaced apart from the central resonator by an offset gap.

14. The plasmonic resonator according to claim 10, the first longitudinal end and the second longitudinal end being disposed at opposite sides with respect to the center of the central resonator.

15. The plasmonic resonator according to claim 11, the silicon substrate being an undoped silicon wafer.

16. The plasmonic resonator according to claim 11, the Fe layer including an oxide layer.

17. A plasmonic resonator system, comprising:
a silicon substrate having a crystal orientation of <100>; and
a plurality of plasmonic resonators on the silicon substrate,
each of the plurality of plasmonic resonators comprising:
a Ti rectangular central resonator on the silicon substrate;
a first Fe curved resonator disposed on the silicon substrate, only at a first side of the Ti rectangular central resonator, and being monolithically formed; and
a second Fe curved resonator disposed on the silicon substrate, only at a second side of the Ti rectangular central resonator, and being monolithically formed,
a first end of the first Fe curved resonator being disposed adjacent to a first longitudinal end of the Ti rectangular central resonator, a second end of the first Fe curved resonator being disposed adjacent to a center of the Ti rectangular central resonator, a first end of the second Fe curved resonator being disposed adjacent to the center of the Ti rectangular central resonator, and a second end of the second Fe curved resonator being disposed adjacent to a second longitudinal end of the Ti rectangular central resonator,
each of the second end of the first Fe curved resonator and the first end of the second Fe curved resonator being spaced apart from the Ti rectangular central resonator by an offset gap,
the Ti rectangular central resonator being a monolithically-formed bar having an upper portion and a lower portion,
the first Fe curved resonator facing the upper portion of the Ti rectangular central resonator, and
the second Fe curved resonator facing the lower portion of the Ti rectangular central resonator,
the first side and the second side being different from each other, and
a cross-section of the Ti rectangular central resonator, taken in a direction parallel to an upper surface of the substrate, being rectangular.

18. An immunosensor, comprising:
the plasmonic resonator system according to claim 17; and
an antibody disposed on the plasmonic resonator system.

* * * * *